(12) United States Patent
Geltner

(10) Patent No.: US 12,207,605 B2
(45) Date of Patent: Jan. 28, 2025

(54) AUTOMATED PLANT TREATMENT SYSTEMS AND METHODS

(71) Applicant: ARUGGA A.I FARMING LTD, Even Yehuda (IL)

(72) Inventor: Iddo Geltner, Even Yehuda (IL)

(73) Assignee: ARUGGA A.I FARMING LTD, Even Yehuda (IL)

( * ) Notice: Subject to any disclaimer, the term of this patent is extended or adjusted under 35 U.S.C. 154(b) by 657 days.

(21) Appl. No.: 17/291,457

(22) PCT Filed: Nov. 7, 2018

(86) PCT No.: PCT/IL2018/051201
§ 371 (c)(1),
(2) Date: May 5, 2021

(87) PCT Pub. No.: WO2020/095290
PCT Pub. Date: May 14, 2020

(65) Prior Publication Data
US 2022/0000051 A1   Jan. 6, 2022

(51) Int. Cl.
*A01G 7/06* (2006.01)
*A01H 1/02* (2006.01)
*G06V 10/10* (2022.01)

(52) U.S. Cl.
CPC .............. *A01G 7/06* (2013.01); *A01H 1/027* (2021.01); *G06V 10/10* (2022.01)

(58) Field of Classification Search
CPC ...... A01H 1/027; A01D 46/005; B05B 1/005; A01G 7/06; A01G 2003/007;
(Continued)

(56) References Cited

U.S. PATENT DOCUMENTS

| 4,922,651 A | 5/1990 | Atkinson et al. |
| 2013/0305600 A1* | 11/2013 | Whaley .................. A01H 1/027 47/1.41 |

(Continued)

FOREIGN PATENT DOCUMENTS

| CN | 108401897 A | 8/2018 | |
| GB | 2133664 A * | 8/1984 | ........... A01D 46/005 |

(Continued)

OTHER PUBLICATIONS

Hiroichi et al., Pollinating Robot Translation, Oct. 13, 2011 (Year: 2011).*

(Continued)

*Primary Examiner* — Brady W Frazier
*Assistant Examiner* — Nicole Paige Maccrate
(74) *Attorney, Agent, or Firm* — FISHERBROYLES, LLP; Roger L. Browdy; James E. Mrose

(57) ABSTRACT

Plant treatment systems and methods are presented. The system comprising a plant treatment apparatus comprising: one or more treatment channels and at least one plant treatment device associated with said one or more treatment channels, said at least one plant treatment device being configured and operable to controllably generate a force field and apply the force field to at least a portion of a plant, said force field comprising at least one pulse, wherein each pulse has a fast rise time, certain duration and amplitude profile, thereby inducing a vibration pattern in the at least portion of the plant, said vibration pattern being characterized by a plurality of vibration frequencies above a predetermined value, to thereby apply treatment to said at least portion of the plant; a sensing system comprising one or more sensors configured and operable to provide sensing signals indicative of a condition of said at least portion of the plant and feedback signals indicative of said vibration (Continued)

pattern, said one or more sensors comprising an optical sensor configured and operable to provide the sensing signals and/or feedback signals indicative of image data of said at least portion of the plant. A control system is configured and operable for data communication with said plant treatment apparatus, to receive and process the sensing signals and/or feedback signals produced by the sensing system, the processing of the sensing signals and/or feedback signals comprising determining the condition of said at least portion of the plant and/or said vibration pattern and operating said at least one plant treatment device to apply and/or adjust said force field to thereby induce the vibration pattern corresponding to the treatment of said at least portion of the plant.

26 Claims, 12 Drawing Sheets

(58) Field of Classification Search
CPC .... A01G 2003/005; A01G 22/00; A01G 7/04; A01G 25/16; A01G 25/165; B64U 2101/40
USPC .......................................................... 47/1.41
See application file for complete search history.

(56) References Cited

U.S. PATENT DOCUMENTS

| | | | |
|---|---|---|---|
| 2015/0027044 A1* | 1/2015 | Redden | A01G 7/06 47/58.1 R |
| 2016/0050852 A1* | 2/2016 | Lee | B25J 9/023 901/41 |
| 2016/0353661 A1* | 12/2016 | Caldeira | A01H 1/027 |
| 2018/0065749 A1 | 3/2018 | Cantrell et al. | |
| 2019/0387687 A1* | 12/2019 | Nitsch | G06T 7/0012 |
| 2020/0120886 A1* | 4/2020 | Geltner | A01G 7/06 |
| 2020/0260675 A1* | 8/2020 | Ran | A01H 1/027 |

FOREIGN PATENT DOCUMENTS

| | | | | |
|---|---|---|---|---|
| JP | S61265032 | | 11/1986 | |
| JP | 63219321 | | 9/1988 | |
| JP | 2002112653 | | 4/2002 | |
| JP | 2004016182 | | 1/2004 | |
| JP | 2011147377 | | 8/2011 | |
| JP | 2011200196 A | * | 10/2011 | ............ A01G 7/06 |
| JP | 2012120472 | | 6/2012 | |
| JP | 2012120472 A | | 6/2012 | |
| JP | 2013135634 | | 7/2013 | |
| JP | 2013150584 | | 8/2013 | |
| JP | 2014045680 | | 3/2014 | |
| WO | 2015013723 A2 | | 1/2015 | |
| WO | 2018175552 A1 | | 9/2018 | |

OTHER PUBLICATIONS

Ohi N., et al., "Design of an Autonomous Precision Pollination Robot", 2018 IEEE/RSJ International Conference on Intelligent Robots and Systems (IROS) 2018.
Notice of Reasons for Refusal issued in Japanese Patent Application No. 2021-525042 (Aug. 25, 2022).
Koganei, Proposal for energy saving in air blowing process, Pulse Blow Series, www.koganei.co.jp, 2023, pp. 1-31.
European Search Report mailed on Jun. 9, 2022 of the corresponding European Patent No. EP18939578.

* cited by examiner

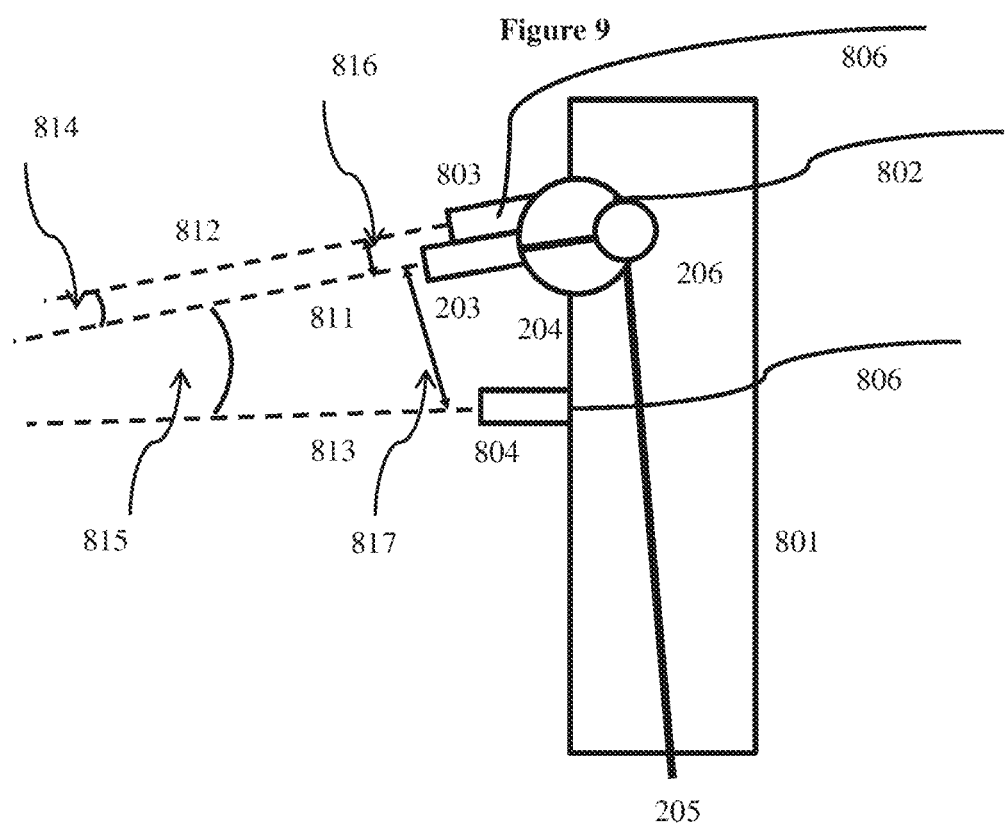

AUTOMATED PLANT TREATMENT SYSTEMS AND METHODS

TECHNOLOGICAL FIELD

The present invention relates to automated treatment of plants in industrial agriculture, such as in green-house grown plants. Specifically, treatment of plants include, for example, targeted mechanical pollination, localized prevention and/or treatment of disease, and inhibition/control of degree of pollination and/or plant growth.

BACKGROUND

Crops need a lot of care, starting from maintaining plants health all over the plant life cycle and followed by pollinating the flowers and insuring healthy crops. With the continuous increase in population and the increased interest in healthy life while decreasing expenses, the traditional ways of agriculture are challenged every day. As known, the majority of crops we eat or use are mainly pollinated by wind or insects. However, for various reasons these natural processes do not exist or do not function optimally. For example, decrease in quantity or disappearance of insects from the farming area, or environmental conditions which limit the ability of insects to move around and pollinate. In greenhouses, for example, wind and insects cannot enter and pollinate. In addition, the growing need for food and cost reduction requires higher efficiency, which subsequently drives farmers to improve fruit set and yield beyond natural pollination.

Depending on conditions and cost, solutions range from manual pollination in various methods, to artificial introduction of insects such as honey-bee hives to farming areas, or industrially grown insects (e.g. the *bombus* bee). In addition, there exist mechanical solutions such as vibrating cables holding the plants, or manually/mechanically vibrating individual plants, trusses or flowers in plants which can self-pollinate.

In many areas, manual pollination is prohibitive due to availability of labor and cost. Bees have several disadvantages too: they require certain environmental conditions, are sensitive to pesticides, can escape (from greenhouses) or pollinate more lucrative crops nearby. They can also transfer viruses and fungi.

US patent application 20160353661 describes a method of pollinating a plant which includes receiving, with a processing circuit, plant data regarding a plant having flowers, and controlling, by the processing circuit, operation of a robotic device to selectively pollinate a portion of the plurality of flowers based on the plant data. The robotic device includes sensors configured to acquire plant data, a pollination device configured to pollinate flowers of a plant, a collection device configured to collect pollen, and a pollination prevention device configured to prevent a flower from being pollinated.

US20180065749 describes methods and systems of pollinating crops, the systems include one or more unmanned vehicles including a pollen applicator configured to collect pollen from a flower of a first crop and to apply the pollen collected from the flower of the first crop onto a flower of a second crop and a sensor configured to detect presence of the pollen applied to the flower of the second crop by the pollen applicator to verify that the pollen collected from the flower of the first crop by the pollen applicator was successfully applied by the pollen applicator onto the flower of the second crop.

GB2133664A discloses an apparatus for imparting motion to a part of a growing plant, the apparatus includes means for providing a pressurized stream of air, such as a compressed air source, feeding into a pressurized chamber which has an outlet provided with a flow modulating valve arranged to provide a pulsed stream of air. An outlet nozzle is arranged to direct the air stream at the part of the plant to be vibrated. The frequency of the pulses exceeds 200 c.p.m. and the apparatus can be used for pollinating plants, for harvesting fruit from plants, or measuring the natural frequency of a plant portion.

JP2011200196 describes an apparatus comprising a traveling device, an identification device for discriminating normal flowers, a vibration device for giving vibration to flowers and performing pollination processing, a pollination processing unit that controls the vibration device so as to give vibration to only the flowers identified as normal flowers in the identification device and a harvesting device for harvesting fruits.

GENERAL DESCRIPTION

The present invention provides novel techniques for treating plants during all of the growth and fruitage cycles including, but not limited to, monitoring plant conditions such as plant health, readiness for pollination and post pollination, and intervening in each of the aforementioned conditions or stages by applying the suitable treatment in order to insure a maximum effectivity and efficiency with respect to yield.

The systems and methods of the present invention are autonomous and based on robotic treatment device(s) that can approach the specific plant or portion of the plant to monitor and treat every plant in a farming area autonomously and without human intervention.

Further, the highly effective systems and methods of the invention are resource, energy and cost efficient in that the treatment applied is targeted and local, down to the sub-plant level and down to a single flower or a specific portion of the flower.

In some aspects, the present invention provides a novel technique for plant treatment by pollinating flowers, specifically automatically pollinating flowers, e.g. for use in industrial agriculture. The system induces vibrations in one or more regions of a plant in order to selectively pollinate one or more flowers on the plant. The one or more regions, referred to occasionally as a portion of the plant, can be for example a plant stem, branch, leaf stalk, leaf, a group of flowers, a flower, or a portion of a flower. The system can detect the flower targets, determine whether they are ready for pollination and determine whether they were not pollinated yet, in order to efficiently and quickly pollinate as much flowers as required in optimal time and energy, and by this cover large amounts of plants.

It is known that *bombus* bees, specifically domesticated for the purpose of pollinating flowers, area good example for optimal pollination process. However, using bees suffers from several downsides as described above. It can be beneficial to emulate the effect of the bees by autonomous clever systems. During activity, the bees induce vibrations in the flowers by holding the flowers and shaking their muscles to induce several (approximately 4-5) pulses of vibrations, each pulse lasting for several tenths of a second, for a total of 2-3 seconds, at frequencies of several hundreds of Hz. The present inventions provides plant treatment systems capable of emulating the "bees effect" while being remarkably efficient.

In some embodiments, plant treatment devices are presented being configured and operable to induce a controlled vibration pattern in the flowers to optimally pollinate the flowers. The controlled vibration field/pattern has the characteristics and parameters, such as the above-mentioned parameters induced by the bees (one or more short-time directional pulses each having a frequency band, i.e. a plurality of frequencies, above a predetermined value, e.g. above 100 Hz), to achieve optimal pollination of the flower based on the plant and flower characteristics, such as kind, size and others. To this end, the plant treatment devices, aimed at pollination, are configured and operable to apply a controlled force/pressure field to a desired portion of the plant (e.g. stem, flowers, etc.), to thereby ultimately generate the controlled vibration pattern in the flowers to be pollinated. Accordingly, the plant treatment devices are configured and operable to apply a controllably variable force field to the portion of the plant. In other words, the controllably variable force field, as used herein, means a force field that induces a vibration pattern having a plurality of frequencies, and it might include one or more force application acts (pulses of force application). In some embodiments, the plant treatment devices are configured to apply the force field through physical contact with the portion of the plant. In some other embodiments, the plant treatment devices are configured to apply the force field without physical contact with the plant, i.e. contactlessly. In the latter case, the plant treatment devices may apply the force field via the application of a controlled air flow towards the portion of the plant. The applied force field, whether by contact or contactlessly, is controlled instantly during the treatment process such that a feedback system feeds the plant treatment system with a sensing data indicative of the vibration pattern occurring in the portion of the plant during the treatment process. It is noted that the word pulse as used herein means a force/pressure applied (with or without contact) having short duration (e.g. lasting for tenths of a second).

In another aspect, the present invention provides systems and methods for plant treatment that include inhibiting over pollination of flowers in order to optimize yield.

In yet another aspect, the present invention provides systems and methods for plant treatment that includes local identification of disease and selectively treating disease.

Autonomous systems and methods, in accordance with the invention, have several important advantages, inter alia: the techniques are not limited by the availability of human labor; not sensitive to temperature and other conditions required for efficient use of bees; not sensitive to pesticides which may kill the bees or require their removal for a certain amount of time; not limited to areas where bees can be used; it does not pose any threat to employees, e.g. stinging by bees; not confined by the fact that bees cannot perform selective pollination in order to prevent over pollination requiring subsequent pruning, and not affected by the fact that bees can also damage flowers if visiting them too many times.

Thus according to a first broad aspect of the present invention, there is provided a plant treatment system comprising:
    a plant treatment apparatus comprising:
        one or more treatment channels and at least one plant treatment device associated with said one or more treatment channels, said at least one plant treatment device being configured and operable to controllably generate a force field and apply the force field to at least a portion of a plant, said force field comprising at least one pulse, wherein each pulse has a fast rise time, certain duration and amplitude profile, thereby inducing a vibration pattern in the at least portion of the plant, said vibration pattern being characterized by a plurality of vibration frequencies including frequencies above a predetermined value, to thereby apply treatment to said at least portion of the plant; and
    a sensing system comprising one or more sensors configured and operable to provide sensing signals indicative of a condition of said at least portion of the plant and feedback signals indicative of said vibration pattern, said one or more sensors comprising an optical sensor configured and operable to provide the sensing signals and/or feedback signals indicative of image data of said at least portion of the plant; and
    a control system configured and operable for data communication with said plant treatment apparatus, to receive and process the sensing signals and/or feedback signals produced by the sensing system, the processing of the sensing signals and/or feedback signals comprising determining the condition of said at least portion of the plant and/or said vibration pattern and operating said at least one plant treatment device to apply and/or adjust said force field to thereby induce the vibration pattern corresponding to the treatment of said at least portion of the plant.

In some embodiments, said at least one of said one or more treatment channels may be configured as a fluid flow channel. The at least one treatment device may be configured and operable to induce the vibration pattern by generating a controlled air flow having a predetermined flow profile towards the at least portion of the plant via the fluid flow channel. The at least one treatment device may comprises an adjustable opening being configured and operable to generate the flow profile of the air flow being a directional and targeted fluid stream that can be directed towards and induces vibration pattern(s) in specific one or more regions in said at least portion of the plant.

In some embodiments, said at least one plant treatment device comprises a vibrating element connected to a contact applicator being configured and operable to contact said at least portion of the plant while vibrating to thereby apply said force field to said at least portion of the plant and induce said vibration pattern therein.

In some embodiments, said at least one plant treatment device may be configured and operable as a plant pollination device, such that said induced vibration pattern is configured to cause pollination of at least one flower within said at least portion of the plant.

In some embodiments, the at least one plant treatment device is configured and operable to apply said at least one pulse having pulse duration of less than 500 milliseconds.

In some embodiments, the at least one plant treatment device is configured and operable to apply said force field to thereby induce the vibration pattern being characterized by a plurality of vibration frequencies, wherein said predetermined value is 100 Hz.

In some embodiments, the at least one plant treatment device is configured and operable to apply the force field and induce the vibration pattern by generating an air flow having a predetermined flow profile, and wherein said at least one plant treatment device comprises a fluid valve having a fast rise time to thereby apply said at least one pulse. The fluid valve may have the rise time of ten milliseconds or less.

In some embodiments, the plant treatment device comprises an adjustable opening configured and operable to generate the flow profile of the air flow being a directional and targeted fluid stream and wherein said fluid valve is positioned adjacent to said adjustable opening.

In some embodiments, the at least one plant treatment device may comprise a filter configured and operable to block microbes, viruses and/or other harmful objects and prevent delivering them to the at least portion of the plant with the air or fluid flow.

In some embodiments, said plant treatment apparatus further comprises an additional plant treatment device comprising a substance delivery device configured and operable to locally deliver or spray one or more treatment substances onto one or more regions of said at least portion of the plant, said treatment substances comprising one or more of the following: a medicament for treating plant disease, a plant hormone inducing plant growth, a pesticide that kills pests, or a plant damaging substance that prevents growth and/or pollination. The substance delivery device may be associated with said one or more treatment channels. The plant treatment device and the additional plant treatment device may be associated with said at least one fluid flow channel. The substance delivery device may be configured and operable to spray pollen towards at least one flower within said at least portion of the plant.

In some embodiments, said at least one plant treatment device comprises a vibrating element, wherein said control system is configured and operable to provide a predetermined profile of the vibrations of the vibrating element by controlling at least one of number, frequency, amplitude and duration of the vibration of the vibrating element.

In some embodiments, said at least one treatment device is configured and operable to induce the vibrations by generating an air flow, wherein said control system is configured and operable to provide the predetermined profile of the air flow by controlling at least one of the following parameters: number of train pulses of air, time gap between train pulses, number of pulses in each train pulse, time gap between two pulses in each train pulse, amplitude of pressure in each pulse, duration of each pulse. In some embodiments, the number of train pulses is one and the number of pulses in the train pulse is not greater than ten.

In some embodiments, the optical sensor and the fluid flow treatment channel are configured with a predetermined fixed relative orientation between axis of line of sight of the optical sensor and axis of propagation of the directional fluid stream. The predetermined fixed relative orientation may comprise an offset and/or angular difference between the axis of the line of sight of the optical sensor and the axis of propagation of the directional fluid stream. The at least portion of the plant being treated may be located within a field of view of the optical sensor. A light collecting plane of said optical sensor may be located adjacently to a fluid exit aperture of said directional fluid stream. The optical sensor and the fluid exit aperture may be fixedly attached.

In some embodiments, said plant treatment apparatus further comprises a pollen transport device configured and operable to collect pollen from a container on vehicle or in farming area and deliver the collected pollen to a pistil of at least one flower within said at least portion of the plant. The pollen transport device may have a patterned surface configured to adhere the pollen being collected to said surface.

In some embodiments, said sensing system further comprises one or more environmental sensors configured and operable to provide the sensing signals indicative of one or more environmental conditions in a vicinity of said at least portion of the plant. The plant treatment apparatus may further comprise an additional plant treatment device comprising an environment conditioning device being configured and operable to modify at least one of temperature and humidity of a surrounding of said at least portion of the plant. The control system may be configured and operable to operate said environment conditioning device. The environment conditioning device may be associated with said one or more treatment channels. The plant treatment device, the substance delivery device and the environment conditioning device may be associated with said at least one fluid flow channel.

In some embodiments, the control system is configured and operable to process the sensing signals and, upon determining that a flower within said at least portion of the plant is to be pollinated, generate corresponding operational data for said at least one plant treatment device to induce said vibrations in the at least portion of the plant.

In some embodiments, wherein the sensing system comprises one or more environmental sensors configured and operable to provide the sensing signals indicative of one or more environmental conditions in a vicinity of said at least portion of the plant, the sensing signals may be indicative of unfavorable conditions for pollination, and the control system may generate operational data for said substance delivery system to deliver or spray a hormone that induces parthenocarpic fruit growth. The sensing signals may be indicative of a disease of said at least portion of the plant or pest in a surrounding of or on said at least portion of the plant, and the control system may generate operational data for said substance delivery system to deliver or spray a medicament or a pesticide respectively.

In some embodiments, the plant treatment system further comprises a sterilization and/or cleaning and/or disinfecting assembly configured and operable to sterilize and/or clean and/or disinfect said at least one plant treatment device. The sterilization and/or cleaning and/or disinfecting assembly may comprise at least one of the following: a hot air blower, a cleaning material applicator and a cleaning or disinfecting or sterilizing material sprayer.

In some embodiments, the plant treatment apparatus comprises a navigation and tracking assembly configured and operable to bring the plant treatment apparatus to a vicinity of said at least portion of the plant to thereby enable treating said at least portion of the plant by the plant treatment system. The navigation and tracking assembly may comprise a robotic arm carrying said plant treatment assembly, and the control system may be configured and operable to controllably move the robotic arm in three dimensions. The navigation and tracking assembly may comprise a ground vehicle configured and operable to controllably transport the plant treatment apparatus to the vicinity of said at least portion of the plant. The navigation and tracking assembly may comprise at least one of the following: one or more optical sensors, and a positioning sensor. The navigation and tracking assembly may comprise an inertial moment unit configured and operable to determine spatial movement path of the robotic arm to thereby optimize plant treatment process time and energy.

In some embodiments, the plant treatment device is mounted on a telescopic arm being controllable by said control system, to thereby adjust distance between said a distal side of said plant treatment device and the at least portion of the plant.

In some embodiments, the control system is configured and operable to determine, based on said sensing signals, whether at least one flower on said portion of the plant is ready for pollination, by comparing said sensing signals with reference data comprising images of flowers ready for pollination, and/or by processing said image data to identify presence of a flower in the image(s) and identify readiness of the flower(s) for pollination by identifying flower parameters indicative of existence or absence of pollination, and/or by utilizing trained artificial intelligence.

In some embodiments, the control system is configured and operable to analyze the sensing signals from at least the optical sensor and determine a condition of said at least portion of the plant while being treated and after the treatment, and generate corresponding feedback data, enabling decision making about modification of at least one parameter of the treatment affecting the vibrations induced in the at least portion of the plant.

In some embodiments, the plant treatment apparatus further comprises a pollination inhibiting device configured and operable to prevent pollination to occur to one or more flowers and/or prevent growth and blossoming of additional flowers within said at least portion of the plant, while minimizing damage to nearby parts of the plant. The pollination inhibiting device may comprise a laser device configured and operable to irradiate said at least portion of the plant with predetermined laser parameters to thereby damage said at least portion of the plant.

In some embodiments, the at least one treatment device is configured and operable as a pollination inhibiting device configured and operable to generate said fluid stream with a predetermined high temperature, while maintaining the fluid stream directionality by controlling size of fluid stream exit, to burn one or more regions of said at least portion of the plant and prevent pollination to occur to one or more flowers and/or prevent growth and blossoming of additional flowers within said at least portion of the plant, while minimizing damage to nearby parts of the plant.

According to another aspect of the invention, there is provided a plant treatment apparatus, comprising:
  one or more treatment channels and at least one plant treatment device associated with said one or more treatment channels, said at least one plant treatment device being configured and operable to controllably generate and apply a force field to at least a portion of a plant, said force field comprising at least one pulse, wherein each pulse has a fast rise time, certain duration and amplitude profile, thereby inducing a vibration pattern in the at least portion of the plant, said vibration pattern being characterized by a plurality of vibration frequencies including vibration frequencies above a predetermined value, to thereby apply treatment to said at least portion of the plant;
  a sensing system comprising one or more sensors configured and operable to provide sensing signals indicative of a condition of said at least portion of the plant, said one or more sensors comprising an optical sensor configured and operable to provide the sensing signals indicative of image data of said at least portion of the plant; and
    a communication utility for data communication with a control system to transmit the sensing signals to the control system and receive from the control system operational data for said at least one plant treatment device to induce vibrations corresponding to the treatment for said at least portion of the plant.

According to yet another aspect of the invention, there is provided a plant treatment apparatus comprising:
  one or more treatment channels and at least one plant treatment device associated with said one or more treatment channels, said at least one plant treatment device being configured and operable to controllably generate and apply a force field to at least a portion of a plant, said force field comprising at least one pulse, wherein each pulse has a fast rise time, certain duration and amplitude profile, thereby inducing a vibration pattern in the at least portion of the plant, said vibration pattern being characterized by a plurality of vibration frequencies including vibration frequencies above a predetermined value, to thereby apply treatment to said at least portion of the plant;
  a sensing system comprising one or more sensors configured and operable to provide sensing signals indicative of a condition of said at least portion of the plant, said one or more sensors comprising an optical sensor configured and operable to provide the sensing signals indicative of image data of said at least portion of the plant; and
    a communication utility for data communication with a control system to transmit the sensing signals to the control system and receive from the control system operational data for said at least one plant treatment device to induce vibrations corresponding to the treatment for said at least portion of the plant.

According to yet another aspect of the invention, there is provided a plant treatment apparatus comprising:
  one or more treatment channels and at least one plant treatment device associated with said one or more treatment channels, said at least one plant treatment device being configured and operable to cause targeted damage to at least a portion of a plant;
  a sensing system comprising one or more sensors configured and operable to provide sensing signals indicative of a condition of said at least portion of the plant, said one or more sensors comprising an optical sensor configured and operable to provide the sensing signals indicative of image data of said at least portion of the plant; and
  a communication utility for data communication with a control system to transmit the sensing signals to the control system and receive from the control system operational data for said at least one plant treatment device to cause damage to said at least portion of the plant based on following one or more conditions of said at least portion of the plant: unrecoverable disease, predetermined number of flowers have been already pollinated. In some embodiments, the one or more treatment channels comprise at least one of the following: laser of predetermined parameters of intensity and/or wavelength, air of predetermined high temperature and flow profile, and substance delivery.

According to another broad aspect of the invention, there is provided a method for plant treatment comprising:
  acquiring sensing data comprising image data of at least a portion of a plant;
  analyzing said sensing data to determine whether one or more flowers on said at least portion of the plant are ready for pollination; and
    upon detecting one or more flowers ready for pollination, pollinate said one or more flowers ready for pollination by applying a force field to said one or more flowers ready for pollination by generating an air flow having a predetermined flow profile comprising at least one air pulse having certain amplitude and duration, thereby inducing a vibration pattern in the at least portion of the plant, said vibration pattern being characterized by a plurality of vibration frequencies including vibration frequencies above a predetermined value.

In some embodiments, the acquiring and analyzing of sensing data further comprising acquiring and analyzing environmental data indicative of environmental conditions in a surrounding of said at least portion of the plant, and determining whether said environmental conditions do not allow pollination, enabling modifying said environmental conditions before pollination. Modifying said environmental conditions before pollination may be as follows:

if said environmental data is indicative of humidity higher than required for pollination, applying hot air to said surrounding or said at least portion of the plant; and if said environmental data is indicative of humidity lower than required for pollination, applying wet air to said surrounding or said at least portion of the plant.

According to yet another aspect of the invention, there is provided a method for plant treatment comprising:

acquiring sensing data comprising image data of at least a portion of a plant;

analyzing said sensing data to determine whether a predetermined number of flowers on said at least portion of the plant have been pollinated; and upon determining that the predetermined number of flowers have been pollinated, inhibiting pollination of other flower(s) or preventing growth and blossoming of other flower(s) on said at least a portion of the plant.

In some embodiments, inhibiting pollination is achieved by one or more of the following:

directing a fluid stream of predetermined temperature, temporal and spatial profiles to at least part of said at least portion of the plant;

delivering or spraying a specific substance to at least part of said at least portion of the plant;

irradiating at least part of said at least portion of the plant with a laser having predetermined parameters corresponding to kind of the plant.

In some embodiments, the at least part of said at least portion of the plant comprises a single flower or a region in a single flower.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 9 illustrates a non-limiting example of mounting of the treatment apparatus together with imaging sensors;

DETAILED DESCRIPTION

Figure 1:
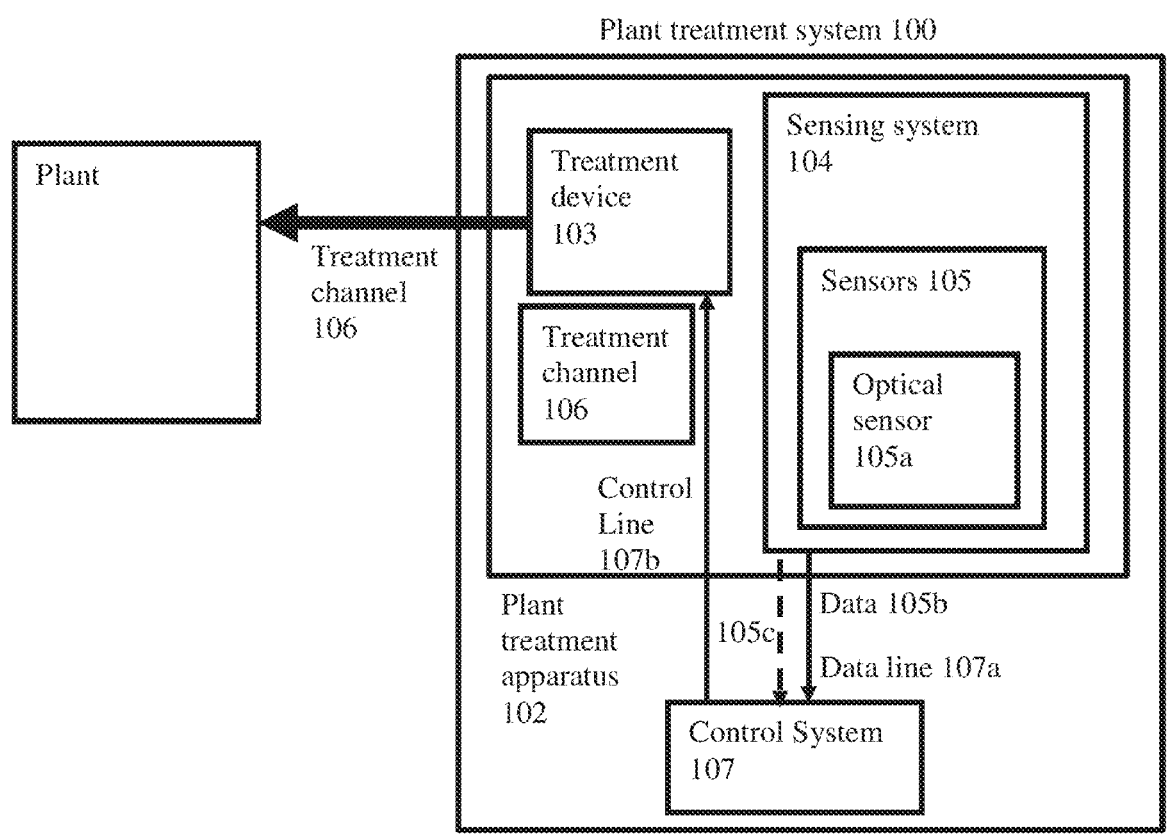
FIG. 1 illustrates by way of a block diagram an exemplary embodiment of a plant treatment system according to the invention.

Reference is made to FIG. 1 that depicts a general schematic diagram of the features of a non-limiting embodiment of a plant treatment system 100 for treating at least a portion of a plant, in accordance with the invention. The plant treatment system 100, includes a plant treatment apparatus 102 and a control system 107 connected to and communicating with the plant treatment apparatus 102, e.g. via data and/or control lines 107a and 107b. The plant treatment apparatus 102 includes one or more treatment channels 106 and at least one plant treatment device 103 associated with the one or more treatment channels. The plant treatment apparatus 102 also includes a sensing system 104 that includes one or more sensors 105 configured and operable to provide, to the control system 107, sensing signals 105b indicative of a condition of the at least portion of the plant.

Accordingly, the plant treatment system 100 is configured and operable to monitor the plant during all of its growth stages, including the stage of flower blossoming, pollination and fruitage, by the sensing system 104, and once a predetermined condition of the plant, relating to one or more of the plant growth stages, is identified, the plant treatment system 100 is configured and operable to apply a corresponding treatment by the at least one plant treatment device 103 associated with one or more treatment channels 106. For example, the plant treatment system 100 identifies, by suitable sensor(s) of the sensing system 104, a condition related to pollination, e.g. whether one or more flowers on the plant are ready to be pollinated and as a result, the plant treatment system 100 operates the at least one plant treatment device 103 in order to pollinate the one or more flowers. In some embodiments, and as will be further detailed below, the plant treatment system 100 can monitor the health of the plant, by suitable sensor(s) of the sensing system 104, and upon identifying that the plant suffers from a specific disease, the plant treatment system operates the at least one treatment device 103 to apply a corresponding treatment to the diseased plant, such as by delivering a suitable drug or medicament.

As described, the sensing system 104 monitors, by its one or more sensors 105, a condition of the plant, generates a corresponding sensing data 105b and sends the sensing data to the control system 107. Additionally, a feedback system consisting of the sensing system 104, the control system 107 and the link 105c, may be included in the plant treatment system 100 and enables acquisition of feedback data 105c, e.g. by an imaging sensor, regarding the plant condition during the treatment process. The control system 107 receives the sensing data and/or the feedback data, via the data line 107a (or a corresponding plurality of data lines—not shown), and processes the sensing/feedback signals to determine the condition of at least portion of the plant, then operates the at least one plant treatment device 103, by generating operational data and sending it via the control line 107b, to apply a corresponding treatment to the at least portion of the plant.

It should be noted that while, in this specific example, the illustration shows that the control system 107 is a separate element, it can be configured in other ways too. For example, the control system 107 can be an integral part of either the sensing system 104 or the at least one treatment device 103 or can be distributed there between. In that case, the data and control lines are merged into one transmission/communication line. Further, it is noted that the control system 107 may be located inside or outside the plant treatment apparatus 102. For example, the control system 107 can run on an external server that communicates with the other elements of the plant treatment system 100 via network, whether wired or wireless network.

The at least one treatment device 103 is configured and operable to apply treatment to the at least one portion of the plant by controllably inducing a vibration pattern/profile in the at least one portion of the plant. The vibration pattern is costumed to the desired kind of treatment to be applied, by controlling, e.g. via the control system 107, the parameters of the profile of the vibration pattern. The at least one treatment device 103 can be configured to apply the vibration pattern to one or more regions in the at least one portion of the plant to thereby achieve the required treatment in the minimum energy and/or time. The vibration pattern/profile, induced in the one or more regions of the at least one portion of the plant, can be applied by the plant treatment device 103 in a contact or contactless manner, as will be further described below.

The vibration pattern/profile induced in the at least portion of the plant should consist of a predetermined range of amplitudes, durations and frequencies, that meet the desired plant treatment action, as will be further described below. For example, to pollinate one or more flowers in a self-pollinating plant, a portion of the plant, or the flower(s) directly, is caused to vibrate at a profile of vibrations that includes a pre-determined range of amplitudes, durations and frequencies. Specifically, as will be described further below, for pollinating flowers, the plant and/or the flower(s) should be vibrated at a range of frequencies, which include frequencies above 100 Hz, and for a limited time, otherwise the flowers may be damaged or the pollination process may not be effective. Optimal pollination of self-pollinating flowers through 'buzz' pollination (which releases pollen through vibration of flowers, either directly or through another plant element that the flowers are attached to) is performed by inducing vibrations in the flowers in a specific manner. As mentioned above, it is known that *bombus* bees, specifically domesticated for this purpose, induce vibrations in the flowers by holding the flowers and shaking their muscles to induce several (approximately 4-5) pulses of vibrations, each for a duration of several tenths of a second, for a total of 2-3 seconds. It is also well known that vibration frequencies should be 100 Hz or higher. These parameters of vibration are essential to produce optimal results—the need to tear the pollen sacks within the flower requires a certain amplitude/intensity and frequency of vibration, and several pulses may be needed to ensure all sacks are torn. However, too many pulses, too long duration of each pulse, and too high amplitude may damage the flower or prevent pollen from sticking to stigma.

As mentioned above, the plant treatment apparatus 102 includes one or more treatment channels 106 which the at least one treatment device is associated with one or more of them. The one or more treatment channels include channel(s) that the plant treatment device 103 uses/requires in order to apply the treatment to the plant. The treatment channel(s) 106 can form an internal part of the plant treatment apparatus or system, or in some cases can be external to it. The treatment channel(s) 106 can be an entry, an intermediate or an exit part with respect to the one or more plant treatment devices 103. It should be noted that, in some embodiments, more than one plant treatment device can be associated with a single, common, treatment channel. In some embodiments, a single plant treatment device can be associated with more than one treatment channel. For example, the treatment channels can include a fluid flow channel configured and operable to provide a flow of fluid, either in gas or liquid or aerosol phase, that the plant treatment device utilizes to apply the treatment. In one specific example, the fluid flow channel is utilized by the plant treatment device in order to generate an air-flow or to blow air towards one or more regions of the at least portion of the plant.

The one or more sensors 105 of the sensing system 104, capable of sensing signals indicative of a condition of the portion of the plant under examination, include at least an optical sensor 105a configured and operable to provide the sensing signals indicative of image data of the at least portion of the plant. The optical sensor 105a can be configured as any optical sensor known in the art. Specifically, the optical sensor 105a can be a camera pointing directly towards the portion of the plant under examination, or can have or be associated with an aperture pointing towards the portion of the plant (e.g. by utilizing an optical fiber while the sensor itself has no direct line of sight with the portion of the plant), or can have a field of view that includes the portion of the plant, etc. The image data can be indicative of a variety of conditions of the portion of the plant that their identification invites a respective treatment by a suitable treatment device. For example, the image data can teach about diseases of the plant, readiness of one or more flowers to pollination, existence of already pollinated flowers, distance between the treatment device and the at least one portion of the plant, vibration pattern occurring during treatment in the flower, etc.

Figure 2:
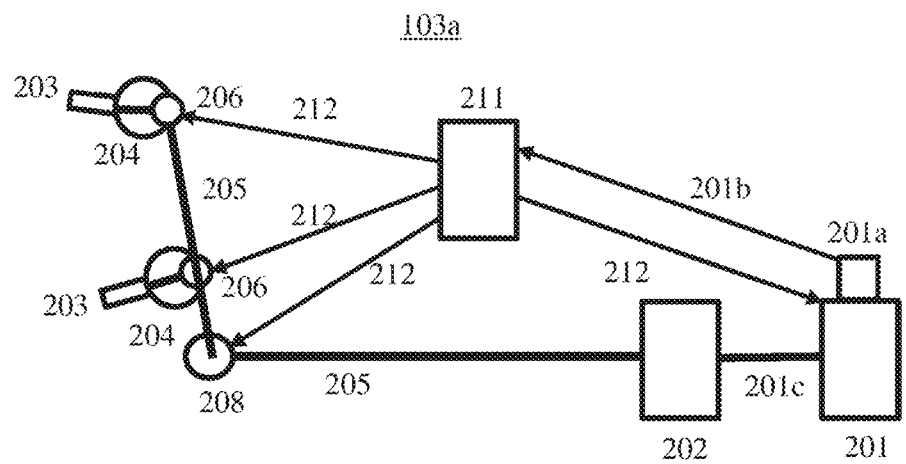
FIG. 2 illustrates a non-limiting example of a treatment apparatus which induces vibration in at least part of a plant by way of air flow.

FIG. 2 depicts a non-limiting example of a plant treatment device 103a which applies a force field to at least a portion of a plant to thereby induce vibration of a predetermined profile in the at least portion of the plant, according to the invention. In this example, the treatment device induces the vibration pattern in the at least portion of the plant contactlessly by applying a force field in the form of a controlled and directional air flow towards the at least portion of the plant. The controlled and directional air flow exiting the distal side of the plant treatment device 103a (the side closer to the treated portion of the plant) and propagating towards the target portion of the plant, e.g. a single flower, is actually a defined air/fluid stream that has predetermined temporal profile (e.g. being configured as a single pulse or as a few pulses with time gaps in between), spatial profile (including direction and volume that can be defined for example by an axis of propagation and stream width), pressure (magnitude) profile, and frequency content (e.g., it can include a plurality of air pulses with equal or different pressure magnitudes with time gaps in between). Therefore, the treatment device of FIG. 2 is associated with a treatment channel that includes a fluid flow channel. The different aforementioned parameters of the air flow are determined, by the control system 107, based on the specific parameters of the plant being treated, where the specific parameters of the plant can be obtained via the sensing system 104. In the described example, the treatment device includes a controller 211 which controls the components of the treatment device through control lines 212. The controller 211 can be part of the control system 107 or can be a direct part of the treatment device 103a as described above. In some embodiments, the controller 211 is configured for data communication with the control system 107 for receiving therefrom operational data indicative of the sensing data provided by the sensing system. A compressor 201 compresses air to a predetermined value or to a value determined by controller 211 which receives the pressure reading from pressure gauge 201a through data line 201b and operates compressor using control line 212. The compressor 201 compresses the air which fills a tank 202 through tube 201c. The tank 202 is connected to fluid flow applicators 203 through tubing 205. Compressed air is delivered to fluid flow applicators 203 upon demand by controlling valves 206 by controller 211 through control lines 212. Air can be delivered to fluid flow applicators 203 independently of each other by controlling each valve 206 separately. Air pressure is further controlled by pressure regulator 208 which is controlled by controller 211 though control line 212.

Air compressor 201 can compress air to the maximum value that the device is planned to use, and by controlling regulator 208 and valves 206, each fluid flow applicator 203 can receive an independently set pressure. The air compressor 201 can be equipped with a microbial filter or other filter (not shown) in order to prevent delivering microbes/viruses or other harmful objects through applicator to plants or portions of plants.

Tubes 205 can be flexible, in order to allow movement of applicators 203 in order to direct air delivery onto required part of plant, by mounting applicators 203 on movable mounts 204, also controlled by controller 211 through control lines 212.

Fluid flow applicators 203 can provide a predetermined profile of air flow (e.g. in the form of a single air pulse, a plurality of air pulses) adjusted to provide the required treatment to the at least portion of the plant. As described, the predetermined profile of air flow can be, for example, a sequence of air pulses by intermittently opening and closing valves 206 at required timings, controlled by controller 211, and by changing air pressure (i.e. magnitude) by regulator 208.

Figure 3:
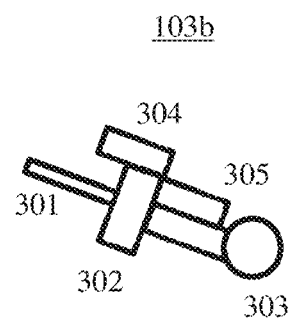
FIG. 3 illustrates a non-limiting example of a treatment apparatus which induces vibration in at least part of a plant by way of contact.

FIG. 3 depicts another non-limiting example of a plant treatment device 103b which applies a force field to at least part of a plant to thereby induce vibration of a predetermined desired profile in the at least part of the plant, by way of direct physical contact with the at least portion of the plant. Accordingly, the treatment device 103b is associated with a treatment channel comprising contact force application. The treatment device 103b includes a contact applicator 301 attached to a vibrating element 302, both connected to a mount 303. The mount 303 can connect the treatment device to a suitable part of the treatment apparatus 102 as will be described below.

The contact applicator 301's length may vary depending on the plant treated. The length may be changed manually by extending or retracting the contact applicator on its holding element attaching it to the vibrating element 302. It can also be controlled by a motor 304 which can vary its length upon commands from a controller 305 that can be configured similarly to controller 211 as described above. The contact applicator 301's rigidity/stiffness can vary depending on target plant. The contact applicator 301 may be rigid if target plant portion to be vibrated is thick/stiff/large/hard to vibrate, or more flexible if portion of plant to be vibrated is small or gentle.

Vibrating element 302 can be constantly vibrating, or can be operated by controller 305 for example upon signal from proximity sensor or force gauge (not shown) placed on the holding element of applicator. Vibration amplitude and frequency may also be changed by controlling vibrating element through controller 305 so as to induce the desired vibration in the plant. For example, during pollination process, in order to induce a vibration pattern of the required parameters such as amplitudes and frequencies (about 100 Hz and more) in the flower(s), the plant treatment device 103b can be configured to continuously contact a portion of the plant, via the contact applicator, while vibrating with corresponding amplitudes and frequencies that are transferred to the plant and cause the desired vibration profile in the flower(s). Alternatively, the plant treatment device 103b can be configured to hit a specific portion of the plant, via the contact applicator 301, once or for a few times, with predetermined amplitude/magnitude(s) of the force and for predetermined time period(s), so as to induce the required vibration profile (in term of amplitude(s) and frequency(ies) in the flower(s) to be pollinated. In the latter case, the contact applicator strikes the portion of the plant for a very short period of time and with a predetermined amplitude, so as to cause the flower(s) to vibrate with a plurality of frequencies, including frequencies above 100 Hz as described above.

Figure 4A:
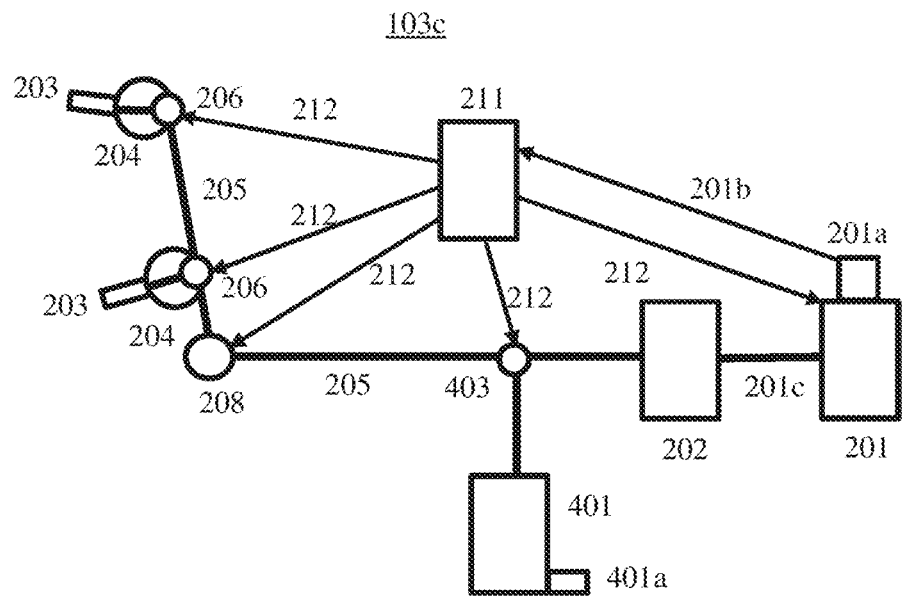
FIGS. 4a-c illustrate three non-limiting examples of a treatment apparatus which delivers directed localized substance or fluid to at least part of the plant.
Figure 4B:
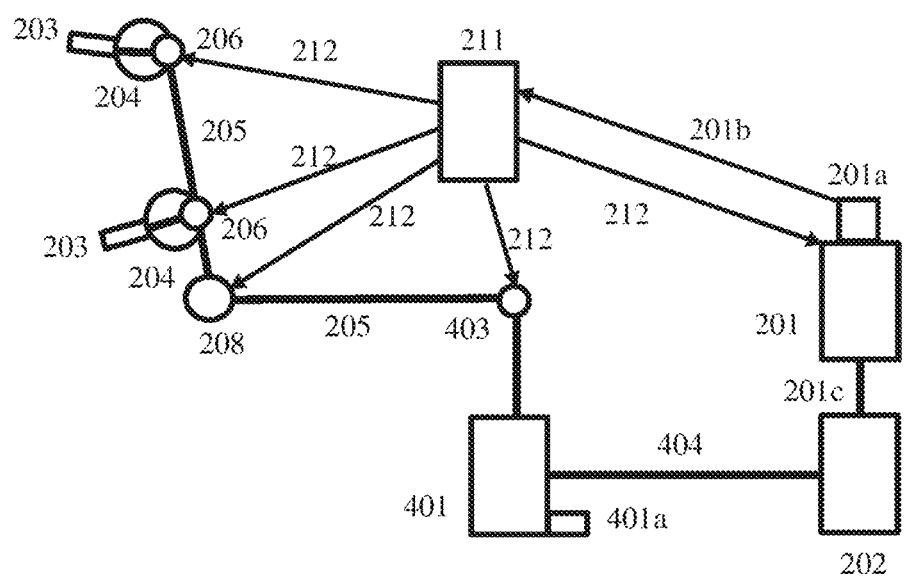
Figure 4C:
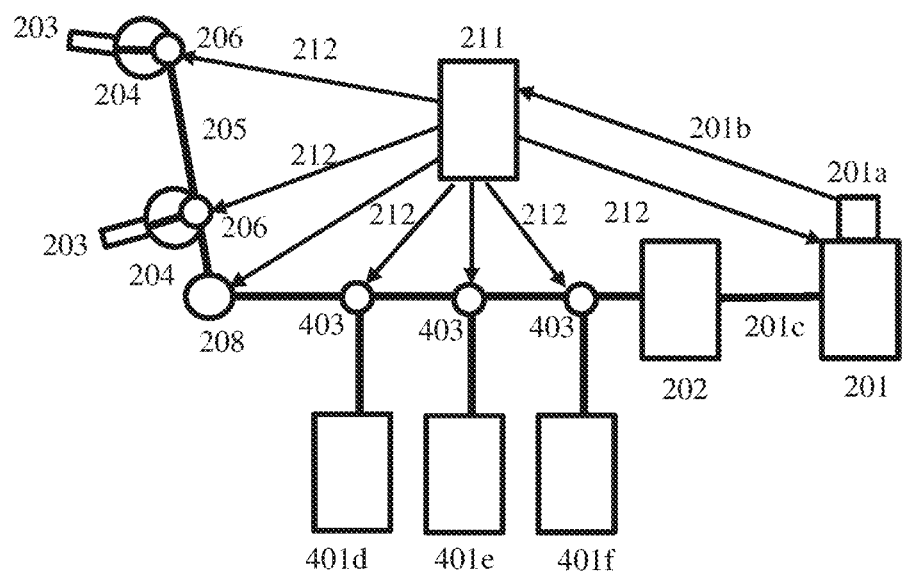

FIGS. 4a-c depict yet another non-limiting example of a plant treatment device 103c for applying a treatment to at least part of a plant, according to the invention. Specifically, the plant treatment device 103c is configured and operable for directed and localized fluid and/or substance delivery to at least a portion of a plant. Accordingly, the treatment device 103c is associated with a treatment channel for dispensing material, and in some embodiments, the treatment channel is a fluid flow channel. The treatment device 103c is similar in some of its features to the treatment device 103a described in FIG. 2. The treatment device 103c includes all the elements of the treatment device of FIG. 2 with an additional fluid reservoir 401. The reservoir 401 is connected to tubes 205 through valve 403, which is controlled by the controller 211 through a control line 212. The reservoir 401 can be filled through connector 401a.

In order to deliver fluids to a portion of the plant, valve 403 is operated such that it allows both pressurized air to flow from tank 202 and fluid from reservoir 401. Together, the mixture of air and fluid are delivered through tubes 205 to fluid flow applicators/apertures 203 by opening valves 206. In some embodiments, reservoir 401 can contain a powder, which is delivered to a portion of the plant in the same manner as the fluid.

Another non-limiting embodiment of the fluid delivery treatment device 103c is described in FIG. 4b. Here, pressurized air from tank 202 is used to pressurize fluid in reservoir 401 through tube 404. The pressure is controlled by compressor 201 which is operated by controller 211. The pressurized fluid in reservoir 401 is delivered to plant through valve 403 which is controlled by controller 211 through control line 212. Reservoir 401 can also be pressurized by connecting pressurized air through connector 401a.

Both non-limiting embodiments described in FIGS. 4a and 4b can be expanded to include more than one reservoir. An example of such embodiment is described in FIG. 4c with 3 reservoirs 401d-f. This embodiment enables the treatment device to deliver for example 3 types of fluid to the plant, either separately or as mixtures, by controlling timing of valves 403 by controller 211 through control lines 212. Similarly, one reservoir 401f may contain a cleaning fluid which will flush the tubing 205, valves 403 and 206, regulator 208 and fluid applicators 203 between the application of the different fluids/materials.

Figure 5:
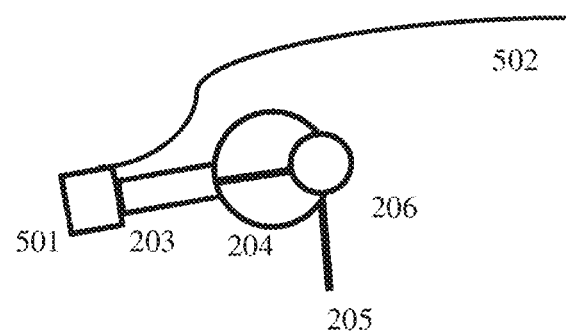
FIG. 5 illustrates a device to control the aperture of the air flow or fluid delivery treatment channel.

FIG. 5 depicts a non-limiting example of an applicator/aperture 203, shown in FIGS. 2 and 4, with an adjustable opening 501 at its distal tip. The figure shows the aperture 203, on its mount 204, with tubing 205 connected through valve 206. Adjustable opening 501 is connected to controller 211 (not shown) through control line 502. When used with system for fluid delivery as described in FIGS. 4a-c, the adjustable opening size can be changed in accordance with the type of fluid. For example, when fluid is more viscous the opening 501 can be enlarged. Opening's size can be changed in order to adjust application of fluid between directed spraying to aerosol. When used with air flow device described in FIG. 2, opening's size can change in order to affect air flow pattern from directed, when opening's size is large (but not larger than the size of the applicator 203 exit), to divergent, when opening's size is smaller than the size of the applicator 203 exit. The size can be changed depending on type of portion of plant to be vibrated, its distance from the applicator 203, or in order to change flow rate or pressure amplitude so as to control amplitude of vibration. When vibration is induced on a large portion of a plant, or when the distance is large, or when amplitude of vibration is large, the opening size needs to be enlarged to increase air flow/intensity/amplitude. When the portion of the plant to be vibrated is close or small, the induced vibration should be gentle and the opening size can be decreased accordingly. In general, opening's size should be kept to a minimum in order to minimize air flow and conserve energy, especially when dealing with a treatment system/device operated on batteries, or when pressurized air is delivered from a reservoir of the treatment system/device.

FIG. 6 depicts another non-limiting example of a plant treatment device configured for inducing vibration in the plant by applying a controlled force field by air flow. This is another example of the ability of the plant treatment device to control the air flow at the output such that the air pulses reach the plant portion with short enough rise time and high enough amplitude, so that frequencies above a predetermined value relating to the plant being treated, e.g. 100 Hz, remain a substantial portion of the frequency content of the pulses, e.g. forming a substantial portion of the energy of the force field applied, thus enabling effective and powerful vibration inducing while maintaining energy conservation. In this connection, it is noted that the expression "rise time", as used herein throughout the text, means the time that it takes for a certain quantity to rise from a first value to a second value. For the purposes of the current invention, the rise time is the time that takes for a quantity, e.g. a force or pressure, to go up from zero up to 90%, or more specifically from 10% to 90%, of its second value (which can be the maximum value the force or the pressure reached). As known in the art, the value of the rise time of a specific quantity and the shape of the pulse define the frequency content of the quantity, i.e. the energy distribution across the frequencies of the quantity. According to the invention, the plant treatment system is configured to generate at least one pulse having a shaped rise time such that the induced vibration pattern includes vibration frequencies above a predetermined value, matching the specifically treated plant, and having a desired energy distribution. It is noted that the frequency content may also include frequencies below the predetermined value but not necessarily. Specifically, if the frequency content includes frequencies below the predetermined value, then it is preferable, for energy conservation, that a substantial portion of the energy of the force field is within the frequencies that are above the predetermined value. Typically, the rise time is short enough to generate in the plant vibration frequencies above a predetermined value corresponding to the plant under treatment, for example, the rise time is in the range of a few milliseconds, for example less than ten milliseconds.

Specifically, the depicted device in FIG. 6 has a valve, that controls the air flow output, located close to the air flow outlet aperture (either aperture 203 or adjustable opening 501), thereby preventing temporal or spatial broadening of the air pulse(s) and by this achieving optimal pollination while saving energy. It should be understood that the distance from the valve or the output aperture (203 or 1401 in this example), whichever controls the pulse, to the at least portion of the plant being treated should be short enough to minimize temporal or spatial broadening of the pulse before reaching the treated portion of the plant, thereby saving energy, and inducing vibration frequencies above a predetermined value. To this end, in some embodiments, the valve is located adjacent to the aperture enabling the distal side of the aperture to be farther away from the plant. In some other embodiments, the valve is located at a specific distance to the aperture, thereby requiring bringing the distal side of the aperture closer to the plant.

As shown in this specific example, the device has an aperture 203 with an adjustable opening 501 at its distal tip. The figure shows the aperture 203, on its mount 204, with tubing 205 connected through valve 206. All these elements have the functionalities as described above. Adjustable opening 501 is connected to controller 211 through control line 502. A valve 1401, connected to controller 211 through control line 1402 is located immediately before the adjustable opening 501 (and accordingly, the distal side of the output aperture can be held at a specific distance from the plant). In this particular embodiment, the valve 206 can be optional, or can be left open or operated in order to let pressurized air flow only to the required apertures if there are multiple apertures. The valve 1401 is operated to prevent the air pulse from broadening in time before reaching the plant portion. Fast valve 1401 can be operated together with adjustable aperture 501 or by itself if its aperture is suitable. The distal tip of the opening 501 can be positioned close to the plant part either by moving arm 801*a* or 801*b* (shown in FIG. 11 below) or mounting on robotic arm 901 (shown in FIG. 10 below) to position it at the optimal distance from the plant part. Another implementation can be by placing the distal edge of the aperture 203 and valve 1401 (with or without adjustable opening 501) on a telescopic structure 1403. The telescopic structure 1403 can be extended or retracted in order to place the most distal side (the opening 501 or the valve 1401) at the right distance from the plant part. The stopper arm can be placed on a linear actuator 1405 which is controlled by controller 211 through control line 1406 that positions the stopper 1404 at the right extension. The telescopic structure can retract automatically by a spring or by moving the stopper 1404 with actuator 1405 back to its retracted position. It is important to retract the distal side to decrease chances of undesirable contact with plants while moving the plant treatment device between plants. The air pulses exit the solenoid close to the desired plant part, minimizing the expansion of the pulse so that it reaches the plant with a fast rise time and enough amplitude. A fixed aperture distance from plant part required to be vibrated is not optimal since both induced vibration frequencies and amplitude(s) must be within a certain range, and since the pulse expands both in time and in space it must be adjusted in each case, and since each inflorescence that needs to be vibrated is structured differently a feedback mechanism is necessary for optimally induced vibrations.

The plant treatment devices illustrated in in FIGS. 2, 3, 5 and 6, together with the control unit 107 and/or controller 211, enable controlling all the characteristics of the non-contact induced vibrations: amplitude, frequency content (e.g. by controlling the rise time and fall time of the air pulse amplitude), duration of each pulse (whether applied by contact or contactlessly), number of pulses, time between pulses. The control of the above listed characteristics can be pre-defined or adjusted upon detection of an object to be vibrated, and optionally adjusted in real-time following feedback from the sensing system 104 monitoring and detecting induced vibration and determining whether the induced vibrations are sufficient. In the case of force field application by air flow, air pressure is created by the apparatus described in FIG. 2 where pressure is controlled by regulator 208. Air pulse train, pulse lengths and number is controlled by solenoids/valves 206 and/or 1401. The frequency content of the air pulse is controlled by the speed of the solenoid/valve 206 and/or 1401 and its distance from the object to be vibrated. The solenoid is preferably small and fast in order to be able to create short rise times. Once the pulse is released from the solenoid/valve it starts broadening in time, therefore the system can additionally control the pulse (and its frequency content) by placing the solenoid/valve at the distal edge of the air opening 203, and by further placing the air opening 203 closer or farther away from the object, e.g. by moving arms. The distance to the object may be determined by a single imaging device, e.g. by determining the size of the object, or by stereoscopic imaging or by LIDAR.

Figure 7:
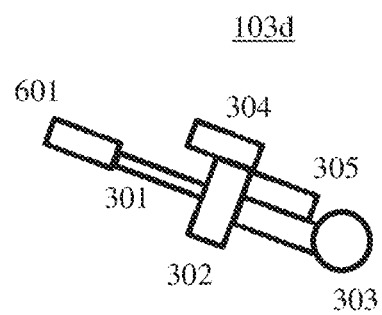
FIG. 7 illustrates a non-limiting example of a treatment system to deliver pollen to the flower by way of contact.

FIG. 7 describes a non-limiting example of a plant treatment device 103*d* for delivery of pollen to at least one flower on a plant. The treatment device 103*d* is similar to the treatment device shown in FIG. 3, with a brush or pad 601 placed at the distal tip of the applicator 301. The brush or pad is brought into contact with the flower on the plant. Pollen preloaded on brush/pad 601, e.g. by immersing the brush/pad in a pollen reservoir, is delivered to a female organ of flower by vibrating brush against organ by operating vibrating element 302. Vibration initiation, duration, frequency and amplitude are controlled by controller 305.

Figure 8A:
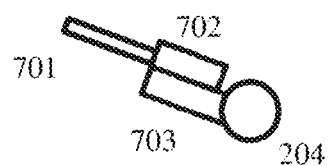
FIG. 8a-c illustrate three non-limiting examples of a treatment apparatus which inhibits pollination to a part of the plant.
Figure 8B:
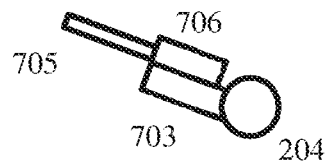
Figure 8C:
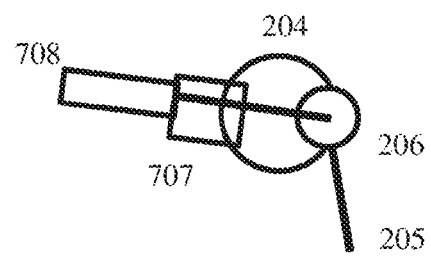

FIGS. 8*a*-8*c* describe non-limiting examples of a pollination-inhibition plant treatment device 103*e* that can be used to damage a portion of the plant. In one embodiment, shown in FIG. 8*a*, the treatment device includes a laser 702, and an applicator 701, through which laser beam is directed towards the portion of the plant, positioned on a holder 703 connected to a mount 204 which can point the beam to the required direction. The laser beam can be pulsed, having long pulses or short picosecond or femtosecond pulses, and can have various wavelengths, e.g. in the IR, visible, or UV spectrum.

In another embodiment, shown in FIG. 8*b*, hot directed air stream is blown towards part of the plant, created by blower 706 and directed towards plant by fluid flow applicator/aperture 705. Size of Opening of applicator/aperture 705 should not be too small (on the order of 1-3 mm) in order for hot air to be directional and by this minimize damage to surrounding portions of the plant.

In yet another embodiment, shown in FIG. 8*c*, the distal tip of the plant treatment device shown in FIG. 2 is configured with heater 707 and applicator/aperture 708. Air is fed through tubes 205 and valve 206 and heated with heater 707 before being directed towards plant through applicator/aperture 708. All components are positioned on mount 204.

FIG. 9 depicts a non-limiting example of a plant treatment apparatus with a plant treatment device and a sensing system according to the invention. Proximal tips of plant treatment devices described in FIGS. 2, 4 and 7 are placed on mount 204. This mount can be positioned on a fixed post 801 as depicted in FIG. 8. The mount 204 can have two angular degrees of freedom in order to point applicator/aperture 203 towards portion of plant to be treated. An imaging device 803, forming one optical sensor of the sensing system 104, can be placed on mount 204 adjacent to aperture 203. Imaging device 803 is positioned relative to aperture with fixed offset 816. This offset can be translational only, i.e. pointing to same direction but shifted, or can have an angular offset 814 as well. If line of sight 812 of imaging device 803 is parallel to pointing direction 811 of aperture 203, the offset is only translational. Another fixed imaging device 804, forming another optical sensor of the sensing system, can be positioned on post 801. This imaging device 804 is offset relative to aperture 203 with offset 817, and angle 815 is the angle between pointing direction 811 of aperture 203 and line of sight 813 of imaging device 804. Angle 815 depends on position of mount 204. Either or both of the imaging devices can be used to point aperture 203 towards portion of plant to be treated. Both imaging devices can send image data through data lines 806 to controller 211. The controller 211 can determine position and distance of portion of plant to be treated and in turn point aperture 203 to target portion of the plant by controlling mount 204 position through control line 802. The positioning of mount 204 can be determined using one imaging device, or both. If offset of aperture and imaging device is fixed, as in the offset of aperture 203 and imaging device 803, and this offset is known to controller 211, then pointing of aperture 203 can be done by pointing imaging device 803 with an offset relative to portion of plant to be targeted. If offset is adjustable, as in the case of aperture 203 and imaging device 804, the distance to target can be measured by image analysis of image data provided by imaging device 804, and with known translational offset 817, controller 211 can point aperture correctly to the targeted portion of the plant. While this requires the additional data of distance, the advantage is that an imaging device located at a large offset from the aperture may see targets not visible to imaging device located adjacent to aperture. Two or more imaging devices can overcome the issue of hidden targets, or at least increase chance of not missing targets. In addition, image data from two or more imaging devices placed with an offset from each other can be analyzed stereoscopically to find the distance to the target.

Figure 10:
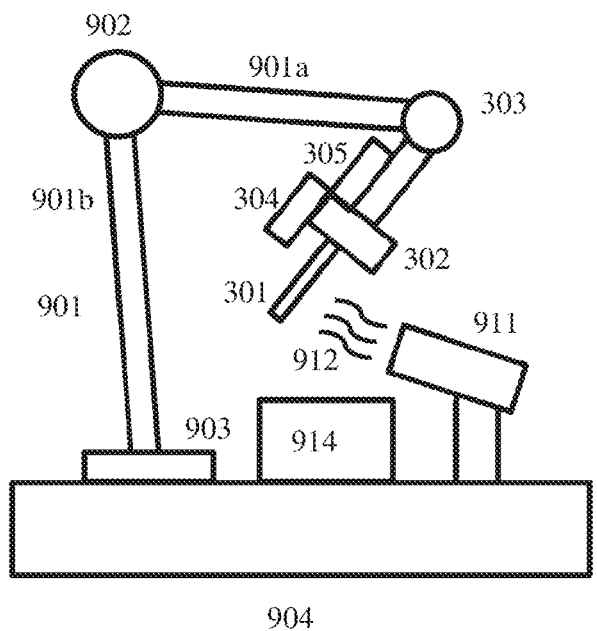
FIG. 10 illustrates a non-limiting example of mounting of the treatment apparatus which induces vibration in at least part of a plant by way of contact, together with a cleaning/sterilizing/disinfecting system.

FIG. 10 depicts an example of mounting the treatment device 103*b* described in FIG. 3. As described above, the treatment device 103*b* is configured and operable to induce vibration on a portion of a plant through contact. The treatment device 103*b* includes the contact applicator 301, its vibrating element 302, motor 304, controller 305 and mount 303. The mount connects the treatment device to a manipulator arm 901, which in this specific example includes two arm sections 901a and 901b, connected with joint 902 and having mount 303 acting as another joint too. The arm 901 is placed on a base 903 which can also act as another joint.

The arm's length and degrees of freedom, determined by the number and lengths of arm sections, joints and their respective degrees of freedom, should be such to enable reaching by contact all required portions of the plant which are planned to be treated, including but not limited to highest and lowest parts of the plant. In addition, the overall reach of the manipulator arm can be such as to allow reaching portions of plant from different angles of approach, for example reaching a leaf from underneath, or reaching a stem from one or more sides. The purpose is both to be able to contact portions of plant at different angles of approach and prevent damage to other plant portions when approaching, or to allow imaging portions of plant from various angles when configuring distal tip with one or more imaging devices.

Figure 6:
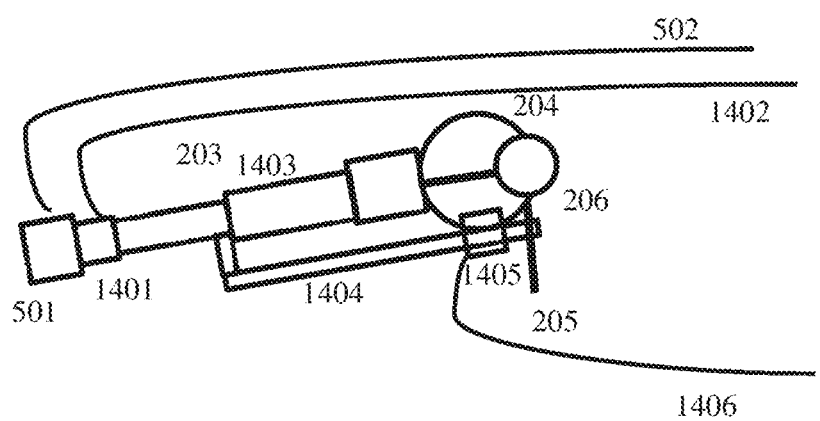
FIG. 6 illustrates another non-limiting example of a treatment device which induces vibration in at least part of a plant by way of controlled air flow.

Also shown in FIG. 10 is a cleaning device 911 intended to clean/disinfect/sterilize applicator 301 or any other part of a treatment device that contacts the plant, such as brush/pad 601 described in FIG. 6. Cleaning device 911 can be configured as a hot air blower blowing hot air 912, or as a dispenser/sprayer to deliver any other material 912 required whether liquid, aerosol or spray, on applicator 301. Cleaning device 911 can be placed on same base 904 together with the manipulator arm 901 so that the arm can place applicator 301 in a fixed position known to be reached by the cleaning material applied by cleaning device 911. Another option is placing a tank 914 with cleaning/disinfecting/sterilizing material in a fixed position on base 904, such that the manipulator arm 901 can dip applicator 301, or any other plant-contacting part of the plant treatment device(s), inside the tank 914 in order to clean/disinfect/sterilize it. The timing of cleaning can be controlled by user or automatically by the control system, according to completion of actions taken by the plant treatment device/apparatus or for example by time elapsed, or by environmental conditions, or by disease and/or pests known to be in the farming area or detected by the sensing system during operation.

Figure 11:
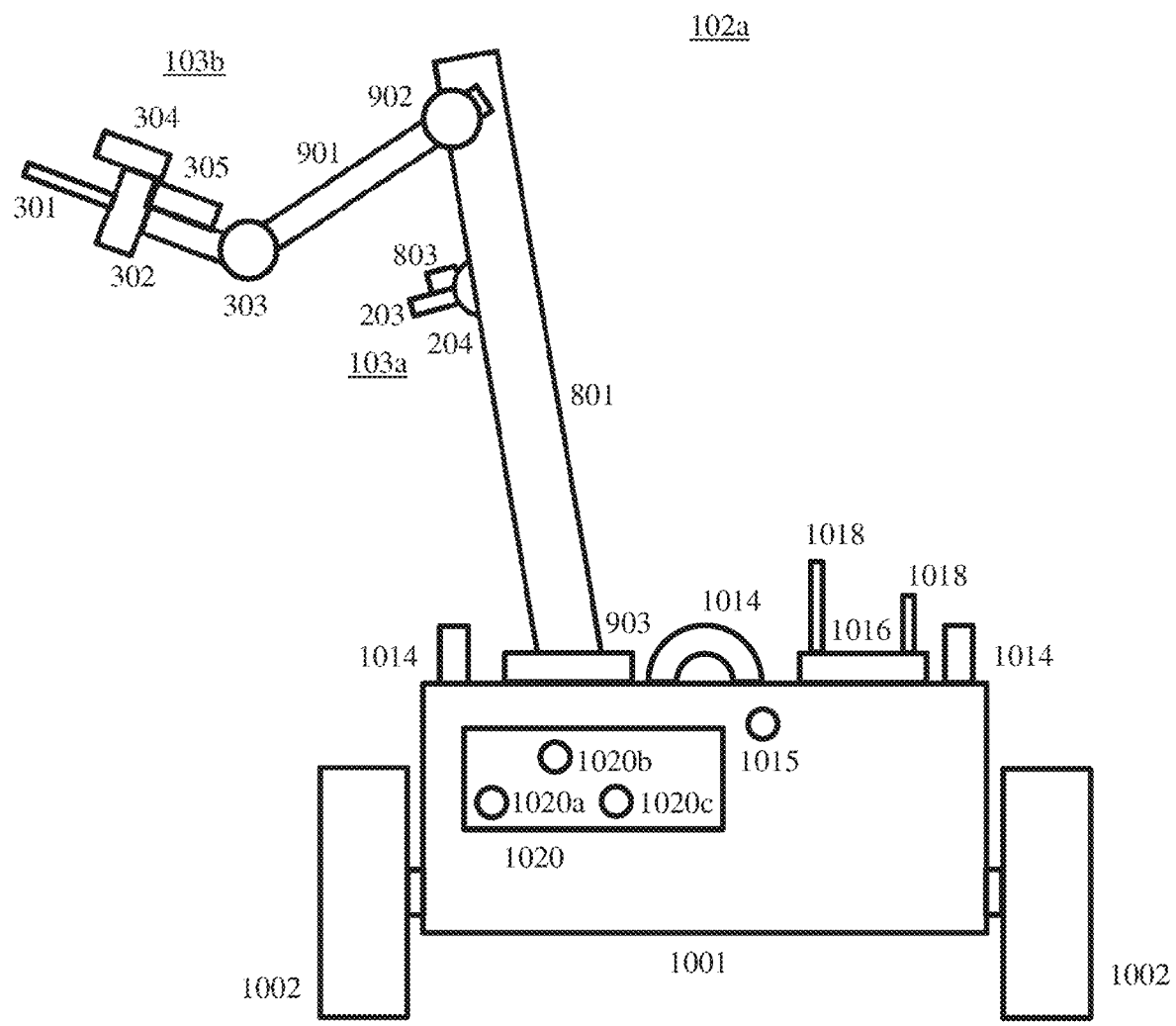
FIG. 11 illustrates a non-limiting example of a navigation and tracking assembly for use with several different treatment devices.

FIG. 11 depicts a non-limiting example of a plant treatment apparatus 102a configured according to the invention. The plant treatment apparatus includes a plurality of plant treatment devices and a sensing system. In this example, one plant treatment device 103b for inducing vibration through contact and one plant treatment device 103a for inducing vibration through air flow are shown and both are mounted on same post 801. Post 801 is placed on base 903, which is described in FIG. 10 and can be static or movable. It should be noted that any combination of the treatment devices described in previous figures can be placed together on post 801. The sensing system includes an optical sensor (imaging device 803) and a set of environmental sensors 1020: temperature sensor 1020a, humidity sensor 1020b and light/ambience sensor 1020c. These sensors can detect environmental conditions in the area surrounding the plant to be treated.

As also shown in the figure, the plant treatment apparatus 102a includes a navigation and tracking assembly 1000 configured and operable to bring the plant treatment apparatus to a vicinity of the at least portion of the plant to thereby enable treating the at least portion of the plant by the plant treatment system. The navigation and tracking assembly includes a movable platform 1001, e.g. a ground vehicle, that can carry the treatment apparatus adjacent to plants to be treated. Vehicle 1001 can be a robotic vehicle, with wheels 1002, operated by motors within vehicle 1001 body. Robotic vehicle can approach plants autonomously using navigation and tracking sensors. For example, robotic vehicle can be equipped with imaging sensors 1014 at front and sides, radar (either MW based or laser based) 1015, and other peripheral sensors as required.

Movement of the robotic vehicle 1001 can be controlled by a dedicated processing unit 1016 and/or by the control system 107. Processing unit 1016 can include wireless communication, an inertial moment unit and GPS, with their respective antennas 1018. The processing unit 1016 collects data from cameras, sensors, inertial moment unit and GPS to guide vehicle 1001 along plants in farmed area. The processing unit controls the motors that operate the wheels 1002 as well as the treatment devices. Wireless communication may be used to communicate with other vehicles to coordinate coverage of farming area or with a central computer. Processing unit 1016 can replace controller 211, or vice versa, to control the treatment apparatus components, namely motors, mounts, valves, imaging sensors, manipulator arms, compressors, and regulators, all described in previous figures, and partially shown in FIG. 11.

While some of the components mentioned are not displayed in FIG. 11 for the sake of clarity, all elements described in previous figures can be placed on vehicle 1001 to support the treatment device(s).

Figure 12:
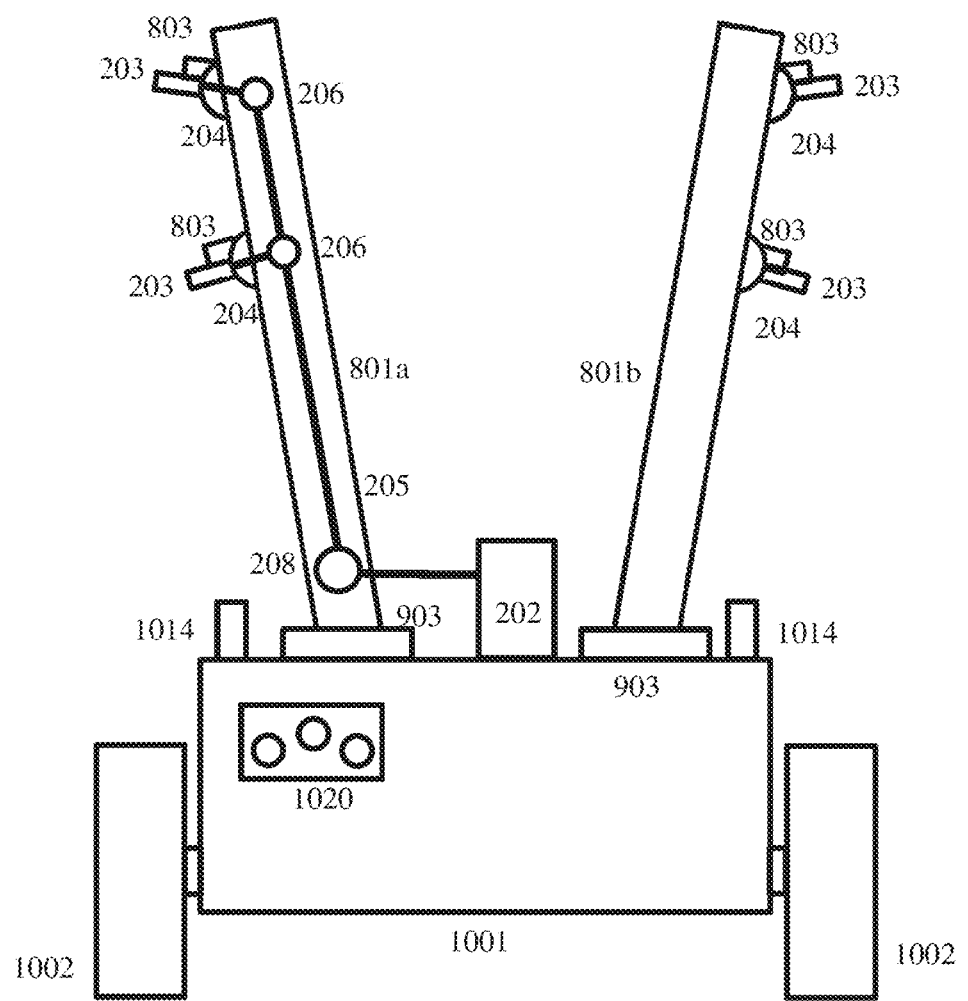
FIG. 12 illustrates a non-limiting example of mounting several treatment apparatuses that induce vibration by way of air flow on a robotic vehicle.

FIG. 12 displays another possible non-limiting setting of a treatment apparatus carried by vehicle 1001. Two posts 801a and 801b that carry one or more treatment devices and optionally sensors of the sensing system, are placed on both sides of the vehicle in order to treat plants on both sides simultaneously or alternately (without the need to turn the vehicle). As shown, different treatment devices can be placed on the same post to enable, for example, treatment of two or more portions of the plant being at different heights simultaneously. If a manipulator arm is placed on a post (not shown), this serves to shorten the required arm extension, thereby increasing the distal tip placement accuracy and reducing the motor strength, size, and cost needed to turn the arm joints. It should be noted that a contact-less vibration inducing treatment device typically moves with 2 degrees of freedom, and contact-based treatment device typically requires at least 3 degrees of freedom (practically may require more to both position applicator in contact with portion of plant, the need to avoid other parts of plant as well as the need to place device at a specific angle relative to portion of plant and the fact that portion of plant which may be a stem which for example can have a random direction/position), which complicates the system.

On each carrying vehicle more than one holding post can be placed in order to treat several plants in parallel, for example one post on each side (to treat plants on both side of row) and/or more than one post one every side of the vehicle to treat two or more consecutive plants simultaneously.

As appreciate, the plant treatment apparatus/system can be a mobile system that can move in a farming area and carry the treatment devices/apparatus adjacent to every plant. The transport/navigation system can be based on wheels, as shown in FIG. 10, or on rails or tracks placed along plant rows in the farming area. The rails can have marked places which can signal the system to stop at each plant. The rails can be placed on the ground or in the air. Together with the control system, location devices such as GPS, and peripheral cameras, the plant treatment apparatus/system can detect plants, register their location and track their treatment in order to return to same portions/flowers or avoid their treatment if they have been treated already.

Figure 13:
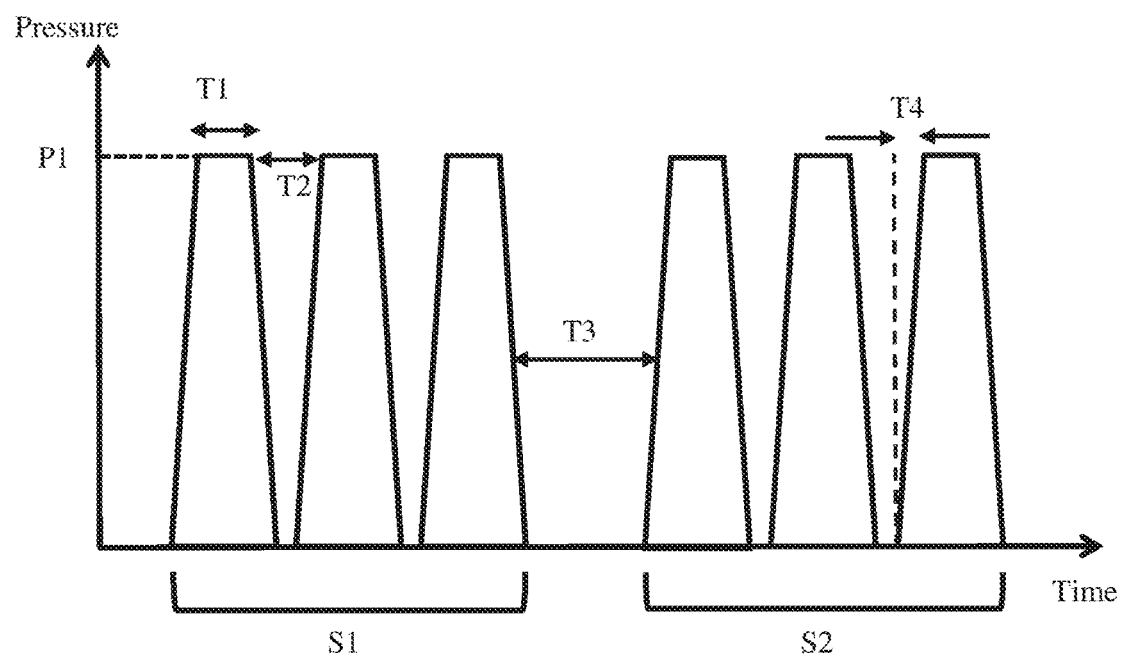
FIG. 13 illustrates a non-limiting example of a pattern of the air flow to induce vibration in at least a portion of a plant.

FIG. 13 shows a non-limiting example of such pulse sequence for use to induce vibration pattern in a treated portion of a plant. The graph depicts the pressure output (Y axis) as a function of time (X axis) of the air exiting the air flow applicators/apertures 203 and/or adjustable opening 501. The pulse sequence can contain one or more air pulses, as required, to generate the desired vibration pattern. The pulse sequence can be determined based on several factors, such as the kind of plant, the portion of the plant to which the force is applied (stem, flower, etc . . . ), the distance from the plant. Additionally, the pulse sequence can be determined online, based on a feedback from the sensing system that provides sensing data regarding the instant vibration pattern being developed in the portion of the plant. The example depicted includes two pulse trains (S1 and S2) with a time separation T3, each pulse train with three pulses of pressure P1, duration T1, gap T2, and rise time T4. Again, the pulse sequence can include one or more pulse trains, with different time separations (T3) between the pulse trains, each pulse train with two or more pulses with a range of durations (T1) and gaps (T2). For example, in one non-limiting embodiment, there can be three trains (S1, S2, S3), with time separation T3=0.5 seconds between the trains, each train with three pulses with gaps T2=0.1 seconds, rise times T4=5 milliseconds and each pulse lasting for T1=0.1 seconds.

As was mentioned, when used in pollination, short rise time of the air pulses is crucial for inducing vibrations at high multiple frequencies (e.g. frequencies>100 Hz). In this case, the rise time of the pulses should be on the order of milliseconds, for example milliseconds or shorter for the frequency content of the pulse to include the required frequencies above 100 Hz. This requires a system as described in FIGS. 2, 5, 6 and 12—a pre-pressurized pressure chamber and regulator and fast solenoid valves to create fast rise time air pulses. To reach fast rise times, solenoid moving element should be small/light and electronics should be designed to support the quick movement of the solenoid. Solenoid linear movement/aperture is on the order of several millimeters, fit for small and flexible air tubes needed for such implementation. Such small solenoids can be placed at the very end of the air aperture 203 or 501, which together with the ability to move air aperture closer to the element to be vibrated, creates a necessary implementation of a system for inducing vibrations required for optimal pollination.

As described above, the vibration of flowers in order to release pollen can be induced by air pressure pulses. This is a contact-less induction/generation of vibration of the flower(s) and/or flower truss or inflorescence in general, in order to induce pollination. Contact-less pollination can reduce chances of disease and virus transfer, and can reduce chances of damage to plant by improper contact. In contrast to non-directional air flow such as air blowers, the invention provides several advantages. Blowers are much more energy consuming, non-controlled, so vibration frequency cannot be controlled, and pressure cannot be adjusted accurately. Due to the large air flow and non-directed and non-localized flow, air blowers can increase chances of spreading diseases, viruses and pests.

The amount of air, the pulse numbers, duration and angle relative to the flowers should match the crop being pollinated, whether by user defined parameters or by pre-defined parameters following automatic detection of flower types, e.g. by vision and applied algorithm in the processing unit.

The strike (by contact) or air pulse sequence should have the following properties: 1) the full sequence should not be more than several seconds long in order to enable treatment of enough plants; 2) pulse length and distance/gap between pulses should enable vibration of flowers at required range of frequencies and amplitudes/magnitude; 3) pulse pressure and air flow rate should be kept to a minimum in order to conserve energy and/or pressure in tank; 4) aperture diameter/opening should not be too small that causes air to diverge and not reach flowers, or too large causing to deplete air too quickly. Valve releasing air to apertures should not be too far from apertures in order to conserve shape of pulse train, and not cause pulses to broaden before exiting aperture. Flow parameters should also be optimized in order not to damage the flowers and/or plant portion.

The plant treatment system/apparatus shown in FIG. 12 can be used for pollinating plants. One possible non-limiting method to pollinate self-pollinating inflorescence of a plant, by using the depicted system, can include the following steps:

1. Bringing vehicle 1001 adjacent to plant by methods described above;
2. View plant with imaging device 803;
3. Analyze images by processing unit 1016 or control system 107 to determine whether at least one flower on portion of plant viewed is ready for pollination. This can be done by a) comparing said image data with reference data showing development stage or growth phase indicative of pollination status of one or more flowers, e.g. a dataset with images of flowers ready for pollination, or b) by processing the image data to identify presence of a flower in the image(s) and readiness for pollination by identifying flower parameters indicative of existence or absence of pollination, such as colour and shape of one or more parts of the flower(s) or c) by utilizing trained artificial intelligence techniques (systems and/or methods);
4. Adjust position of applicator/apertures 203 to point at the required portion of plant by controlling mounts 204 as described above with regards to FIG. 9, by adjusting axis/line of fluid/air stream 811 according to image as seen by imaging devices 803 and/or 804 taking into account their respective offset from aperture 203;
5. Set vibration parameters (pressure, number and amplitude of pulses, each pulse duration and gaps between them) according to portion of plant to be vibrated as viewed by imaging devices and/or according to pre-defined values defined per portion of plant and/or distance to portion of plant and/or other parameters;
6. Release air pulse sequence to controllably vibrate the portion of plant.

In addition to the pollination method described above, once the air pulse sequence was delivered, the imaging device/camera can detect the flower vibration and if not meeting expected amplitude and/or frequency the vibration pattern can be adjusted (i.e. a feedback mechanism) in one of the following: pressure can be increased/decreased by controlling regulator, pulse duration and time gap between pulses can be changed in a train pulse, or the pulse number in a train pulse or the train pulse number, in order to change quantity, frequency and amplitude of vibrations. Pulse direction can also be changed. Instead of pointing to main inflorescence axis (rachis) or larger stem of plant in the aim of vibrating several inflorescences together and to vibrate all flowers together, pulses can be directed to individual flowers.

In order to prevent the need for pruning, the plant treatment system can include communication with an operator (by wireless communication or direct interface to the system) in order to predefine the exact plant being pollinated and focus the algorithm and improve its detection of targets as well as determine the amount of flowers that should be pollinated in each inflorescence or the total in each plant. Additionally, the system can be programmed to detect the plant by itself and have predefined parameters for the number of flowers to pollinate.

The plant treatment system/apparatus can use GPS or visual cues to record (from the set of cameras) the exact position of each visited plant and its flower status for later reference and reporting to farmer. The apparatus can also utilize signs/marks placed in the greenhouse (e.g. barcode sign per plant or row). The cameras can be hyper frequency or any type of camera, e.g. IR, and can have additional illumination in various wavelengths to enhance visibility and detection ability.

As described, the plant treatment system can be equipped with temperature, humidity and light sensors (FIG. 11, 1020a-c), or communicate with sensors placed in the farming area, and automatically determine whether to initiate or stop plant treatment (e.g. pollination) according to pre-defined parameters for each crop (following automatic detection of the crop being pollinated) or user defined settings.

When the plant treatment system/apparatus is equipped with environmental sensors providing environmental data about the plant surrounding, a method for pollinating inflorescences based on environmental data can include the following steps:
1. Collect environmental data from farming area;
2. if conditions fit vibration induced pollination then system can use treatment device(s) that utilizes air pulses;
3. if conditions do not fit such vibration induced pollination, plant microenvironment can be preconditioned:
3a. if conditions are too dry, air can be humidified by the plant treatment device described in FIG. 4a for example, where one reservoir can contain water;
3b. If conditions are too humid, relative humidity can be reduced by heating air applied to portion of plant treated by employing a heating element (as described in FIG. 8c);
4. if conditions do not allow release of pollen by vibration, and preconditioning components are not available, but pollen can attach to female organ, pollen can be locally and directionally applied by the treatment device described in FIGS. 4a-c, where one reservoir contains pollen, and/or pollen can be administered by a contact based vibrating treatment device as described in FIG. 7.
5. if conditions do not allow pollen to attach to female organ, a treatment device such as described in FIGS. 4a-c can be used to spray plant hormones on flowers in order to induce growth of parthenocarpic fruits. Localized and directional administration of plant hormones is crucial since it is necessary to hit exact location of female organ in flowers, it reduces quantities both for saving purposes and since large amounts of hormones can damage plants.

The plant treatment system can selectively pollinate flowers. By visual cues from a set of imaging devices, or a combination of cameras and location determination by GPS or other method, the system will identify flowers on each plant, determine whether each flower is ready for pollination or was pollinated, determine whether a predefined number of flowers was already pollinated on the specific inflorescence. The system will then determine whether to pollinate a specific flower. Depending on the pollination method, the system will target only the flowers to be pollinated. If the pollination device utilizes vibration, as in FIG. 3, selective pollination can be performed by placing the vibrating device adjacent to the flower and setting vibration amplitude such that adjacent flowers will not be pollinated. If the flowers are clustered, the vibration can be timed when the right number of flowers is ready for pollination by visually determining the state of all flowers in the cluster. The same can be performed with the air-pressure method (FIG. 4) and pollen or hormone spray method described above. This method is reversible, i.e. if a different number of flowers must be pollinated, the device can return to the plant and pollinate additional flowers.

In one embodiment of the plant treatment apparatus, described in FIG. 3, a vibrating element can be used for pollination of self-pollinating flowers that require vibration to release their pollen onto the female organ. The vibrating amplitude and frequency can change according to user definition or by pre-defined parameters following automatic detection of flower types by vision and algorithm in the processing unit. The placement of the vibrating element must also match the crop being pollinated. A set of cameras, on the vehicle and/or on the extension arm/post holding the plant treatment device and on the tip of the device will guide the system to place the vibrating element at the exact position of placement, whether at the base of each flower, at the rachis of the inflorescence, or at a branch holding several inflorescences.

Another embodiment of a plant treatment apparatus for pollinating flowers can be based on a brush that is placed on a distal tip of a manipulator arm (FIG. 7) and vibrating tip 301. The arm can guide the brush to a pollen reservoir on the vehicle or in places in the field in order to place pollen on the brush. The brush can then be guided, as is the vibrating tip, to pollinate flowers by placing the brush next to the female organ of the flower and gently rubbing (by vibration) the brush against the organ.

Referring back to FIG. 8, several examples of pollination inhibiting apparatuses are described. By placing such an apparatus on a vehicle as described in FIGS. 11 and 12, by itself or together with other devices described above, portions of a plant can be damaged intentionally. For example, with a laser placed adjacent to imaging device, once the number of required flowers was pollinated, the rest can be intentionally damaged in order to prevent their pollination later. Depending on plant, the portions to be damaged in order to inhibit pollination may vary. For example, a self-pollinating flower can be inhibited by damaging either its male or female organs.

Figure 14:
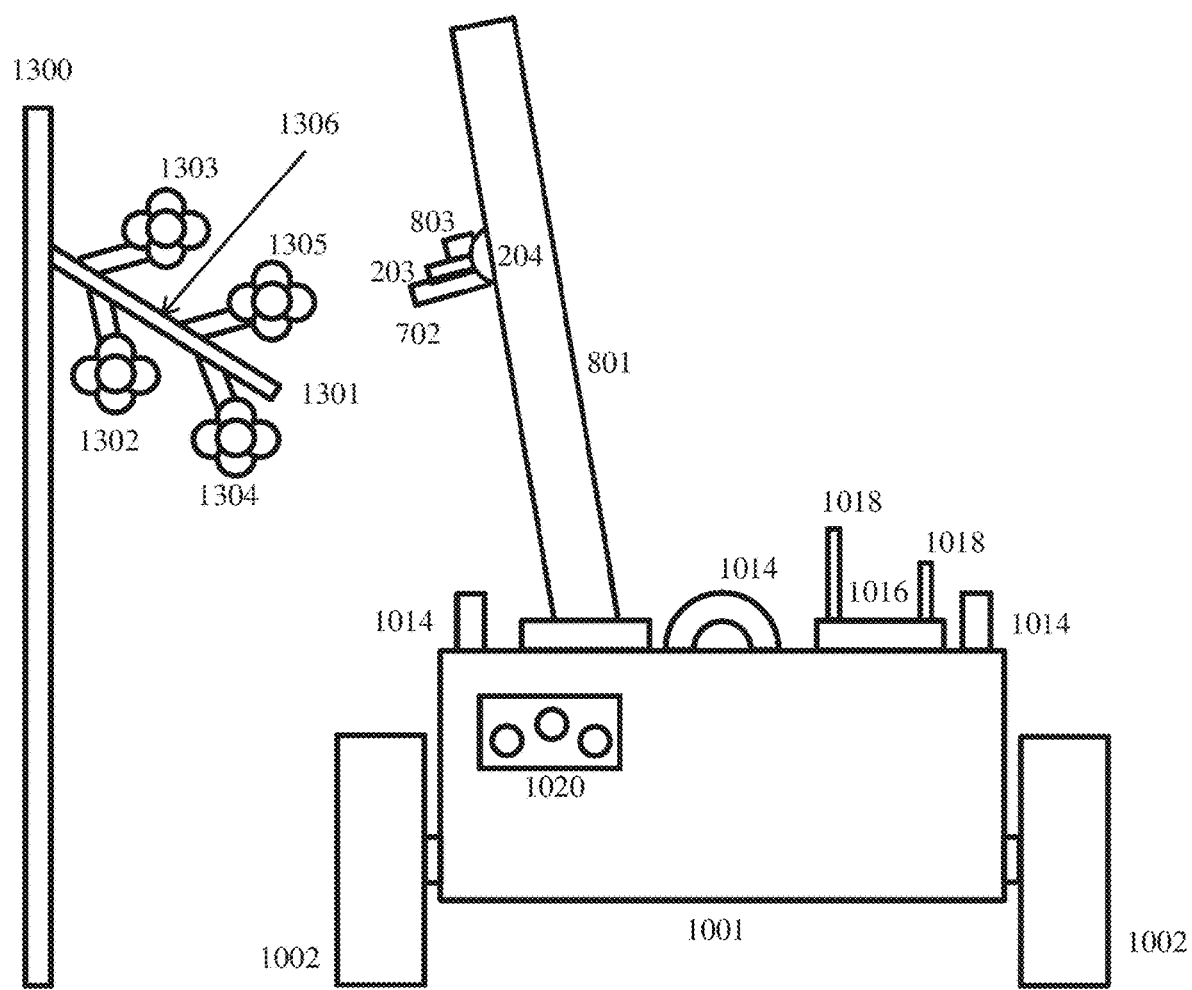
FIG. 14 illustrates a non-limiting example of a pollination inhibition apparatus mounted on a robotic vehicle.

FIG. 14 depicts a non-limiting example of such a pollination inhibiting system. Portion of a plant 1300 is shown. Laser 702 is placed adjacent to air flow applicator/aperture 203, and both pointed by mount 204. The laser can be pointed to individual flowers 1302-1305, or to a location along the rachis 1301 that will damage all flowers beyond a point 1306 (i.e. flowers 1304 and 1305) and prevent from additional flowers to develop on the rachis. This prevents need for pruning since pollination can also occur spontaneously or naturally by wind and insects or movement of plant by farm personnel. Similarly, the damage can be done by hot air (from the heating mechanism described above, set to temperatures which can be pre-defined per type of plant, flower, flower status and/or environmental conditions, as detected by system's imaging devices and/or environmental sensors and are analyzed by processing unit 1016 or control system 107), or by placing a damaging material in the tank and spraying the flowers accurately from close range without damaging other flowers. This requires an apparatus for directed localized substance/fluid delivery as described in FIG. 4. Both directed and localized substance delivery and directed and localized hot air delivery, together with control of quantity of substance or heat of hot air stream, can minimize damage to surrounding flowers and portion of plant or surrounding plants. Similarly, laser energy can be minimized to pre-defined values per type of plant, flower, flower status and/or environmental conditions, as well as setting laser spot size on target to several millimeters or less (depending on exact inflorescence targeted) in order to prevent damage to surrounding portions of plant, since flower organs to be targeted and rachis of inflorescence are on the order of several millimeters.

With multiple cameras existing on the various mounts and posts, each plant can be viewed from many angles and heights up close. This enables detecting pest or diseases. The tank 401 described above (shown in FIGS. 4*a-c*) can contain other treatment materials (e.g. pesticide) and the air pressure mechanism can be used to spray it or other materials for local and efficient treatment of pests, diseases, fungi etc. The system can notify user on the finding and its treatment, and in subsequent visits, since the system registers location of each plant, the status of the disease or pest can be updated in order to ensure that the problem was treated. When system is as described in FIG. 4*c*, i.e. consisting of several tanks, several materials can be placed on the same vehicle, and several diseases or pests detected can be treated.

The invention claimed is:

1. A plant treatment system comprising:
   a plant treatment apparatus comprising:
      at least one plant treatment device comprising one or more treatment channels each configured as a fluid flow channel comprising a fluid flow applicator associated with a controllable fluid valve and a fluid pressure regulator, said fluid flow channel being configured and operable to deliver compressed air to the fluid flow applicator by the controllable fluid valve and to control air pressure by the fluid pressure regulator to generate a controlled air flow having a predetermined profile and being a directional and targeted air flow towards specific one or more regions in at least a portion of a plant being treated, to controllably apply a force field to said at least a portion of the plant, said controllable air flow comprising one or more air pulses, wherein each of said one or more air pulses has certain duration and has a predetermined rise time of the air pressure from a first minimal pressure value to a second maximal pressure value controlled by a speed of opening of the controllable fluid valve and defining frequency content of the pulse and amplitude profile, such that said directional and targeted air flow thereby induces a vibration pattern in the at least portion of the plant, such that the air pulses, inducing said vibration pattern, reach the at least portion of the plant with a predetermined rise time and predetermined amplitude providing the vibration pattern characterized by a plurality of vibration frequencies above a predetermined value, to thereby apply treatment to said at least portion of the plant; and
      a sensing system comprising one or more sensors configured and operable to provide sensing signals indicative of a condition of said at least portion of the plant and feedback signals indicative of said vibration pattern, said one or more sensors comprising an optical sensor configured and operable to provide the sensing signals and/or feedback signals indicative of image data of said at least portion of the plant; and
   a control system configured and operable for data communication with said plant treatment apparatus, to receive and process the sensing signals and/or feedback signals produced by the sensing system, the processing of the sensing signals and/or feedback signals comprising determining the condition of said at least portion of the plant and/or said vibration pattern and operating said controllable fluid valve and the fluid pressure regulator of the at least one plant treatment device to apply and/or adjust said force field to minimize expansion of the air pulses so that the air pulses reach the at least portion of the plant with predetermined fast rise time and predetermined amplitude to thereby induce the vibration pattern, characterized by the plurality of vibration frequencies above the predetermined value, corresponding to the treatment of said at least portion of the plant.

2. The plant treatment system according to claim 1, wherein the optical sensor and the fluid flow channel are configured with a predetermined fixed relative orientation between axis of line of sight of the optical sensor and axis of propagation of the directional fluid stream.

3. The plant treatment system according to claim 2, having at least one of the following configurations:
   said predetermined fixed relative orientation comprises an offset and/or angular difference between the axis of the line of sight of the optical sensor and the axis of propagation of the directional fluid stream;
   said at least portion of the plant being treated is located within a field of view of the optical sensor.

4. The plant treatment system according to claim 2, wherein said predetermined fixed relative orientation comprises at least one of an offset and an angular difference between the axis of the line of sight of the optical sensor and the axis of propagation of the directional fluid stream, the system being characterized by at least one of the following:
   said at least portion of the plant being treated is located within a field of view of the optical sensor;
   a light collecting plane of said optical sensor is located adjacently to a fluid exit aperture of said directional fluid stream; said optical sensor and said fluid exit aperture are fixedly attached.

5. The plant treatment system according to claim 1, wherein said at least one plant treatment device is configured and operable as a plant pollination device, such that said induced vibration pattern is configured to cause pollination of at least one flower within said at least portion of the plant, said at least one plant treatment device being configured and operable to carry out at least one of the following:
   apply said at least one pulse having pulse duration of less than 500 milliseconds;
   apply said force field to thereby induce the vibration pattern being characterized by the plurality of the vibration frequencies above 100 Hz;
   apply the force field and induce the vibration pattern by generating the air flow having the predetermined flow profile, said at least one plant treatment device comprising a filter configured and operable to block microbes, viruses and/or other harmful objects and prevent delivering them to the at least portion of the plant with the air or fluid flow.

6. The plant treatment system according to claim 5, wherein said controllable fluid valve has the rise time from its closed to opening state to thereby apply said at least one pulse, said at least one plant treatment device being characterized by at least one of the following:
said fluid valve has the rise time of ten milliseconds or less;
said fluid flow applicator comprises an adjustable opening configured and operable to generate the flow profile of the air flow being the directional and targeted fluid stream, said controllable fluid valve being positioned adjacent to said adjustable opening.

7. The plant treatment system according claim 1, wherein said plant treatment apparatus further comprises an additional plant treatment device comprising a substance delivery device configured and operable to locally deliver or spray one or more treatment substances onto one or more regions of said at least portion of the plant, said treatment substances comprising one or more of the following: a medicament for treating plant disease, a plant hormone inducing plant growth, a pesticide that kills pests, or a plant damaging substance that prevents growth and/or pollination;
a pollen transport device configured and operable to collect pollen from a container on vehicle or in farming area and deliver the collected pollen to a pistil of at least one flower within said at least portion of the plant;
a navigation and tracking assembly configured and operable to bring the plant treatment apparatus to a vicinity of said at least portion of the plant to thereby enable treating said at least portion of the plant by the plant treatment system; and
a pollination inhibiting device configured and operable to prevent pollination to occur to one or more flowers and/or prevent growth and blossoming of additional flowers within said at least portion of the plant, while minimizing damage to nearby parts of the plant.

8. The plant treatment system according to claim 7, wherein said substance delivery device is associated with said one or more treatment channels, said plant treatment device and said additional plant treatment device being associated with said at least one fluid flow channel.

9. The plant treatment system according claim 1, wherein said control system is configured and operable to provide the predetermined profile of the air flow by controlling at least one of the following parameters: a number of the air pulses in each of at least one train of air pulses, a time gap between the at least one train of air pulses and another train of air pulses, a number of trains of air pulses, a time gap between two air pulses in the at last one train of air pulses, an amplitude of pressure in each air pulse, a duration of each air pulse.

10. The plant treatment system according to claim 9, wherein said number of trains of air pulses is one and wherein said number of air pulses in the train is not greater than ten.

11. The plant treatment system according to claim 1, wherein said sensing system further comprises one or more environmental sensors configured and operable to provide the sensing signals indicative of one or more environmental conditions in a vicinity of said at least portion of the plant.

12. The plant treatment system according to claim 11, wherein said plant treatment apparatus further comprises an additional plant treatment device comprising an environment conditioning device being configured and operable to modify at least one of temperature and humidity of a surrounding of said at least portion of the plant.

13. The plant treatment system according to claim 1, wherein said at least one treatment device is configured and operable as a plant pollination device, such that said induced vibration pattern is configured to cause pollination of at least one flower within said at least portion of the plant.

14. The plant treatment system according to claim 1, wherein said fluid flow applicator comprises an adjustable opening.

15. The plant treatment system according to claim 1, wherein said at least one plant treatment device has at least one of the following configurations:
(i) said at least one plant treatment device further comprises a vibrating element connected to a contact applicator and being configured and operable to contact said at least portion of the plant to thereby further apply the force field to said at least portion of the plant and induce the vibration pattern therein,
(ii) said at least one plant treatment device is configured and operable as a plant pollination device, such that said induced vibration pattern is configured to cause pollination of at least one flower within said at least portion of the plant.

16. The plant treatment system according to claim 1, wherein said plant treatment apparatus further comprises an additional plant treatment device comprising a substance delivery device configured and operable to locally deliver or spray one or more treatment substances onto one or more regions of said at least portion of the plant, said treatment substances comprising one or more of the following: a medicament for treating plant disease, a plant hormone inducing plant growth, a pesticide that kills pests, or a plant damaging substance that prevents growth and/or pollination, wherein said substance delivery device has at least one of the following configurations:
said substance delivery device is associated with said one or more treatment channels;
said substance delivery device is configured and operable to spray pollen towards at least one flower within said at least portion of the plant.

17. The plant treatment system according to claim 1, wherein said at least one plant treatment device additionally comprises a vibrating element connected to a contact applicator being configured and operable to contact said at least portion of the plant to thereby apply an additional force field to said at least portion of the plant and induce a vibration pattern therein, said control system being configured and operable to provide a predetermined profile of the vibrations of the vibrating element by controlling at least one of number, frequency, amplitude and duration of vibrations of the vibrating element.

18. The plant treatment system according to claim 1, wherein the control system is configured and operable to carry out at least one of the following:
process the sensing signals and, upon determining that a flower within said at least portion of the plant is to be pollinated, generate corresponding operational data for said at least one plant treatment device to induce said vibrations in the at least portion of the plant;
analyze the sensing signals from at least the optical sensor and determine a condition of said at least portion of the plant while being treated and after the treatment, and generate corresponding feedback data, enabling decision making about modification of at least one parameter of the treatment affecting the vibrations induced in the at least portion of the plant.

19. The plant treatment system according to claim 1, wherein said plant treatment apparatus further comprises an additional plant treatment device comprising a substance delivery device configured and operable to locally deliver or spray one or more treatment substances onto one or more regions of said at least portion of the plant, said treatment substances comprising one or more of the following: a medicament for treating plant disease, a plant hormone inducing plant growth, a pesticide that kills pests, or a plant damaging substance that prevents growth and/or pollination, said sensing system having at least one of the following configurations:

said sensing system comprises one or more environmental sensors configured and operable to provide the sensing signals indicative of one or more environmental conditions in a vicinity of said at least portion of the plant, wherein said sensing signals are indicative of unfavorable conditions for pollination, and wherein said control system generates operational data for said substance delivery system to deliver or spray a hormone that induces parthenocarpic fruit growth; and said sensing signals are indicative of a disease of said at least portion of the plant or pest in a surrounding of or on said at least portion of the plant, and wherein said control system generates operational data for said substance delivery system to deliver or spray a medicament or a pesticide respectively.

20. The plant treatment system according claim 1, further comprising at least one assembly configured and operable for carrying out at least one of sterilization cleaning and/or disinfecting said at least one plant treatment device, said at least one assembly comprising at least one of the following: a hot air blower, a cleaning material applicator and a cleaning or disinfecting or sterilizing material sprayer.

21. The plant treatment system according to claim 1, wherein said plant treatment apparatus comprises a navigation and tracking assembly configured and operable to bring the plant treatment apparatus to a vicinity of said at least portion of the plant to thereby enable treating said at least portion of the plant by the plant treatment system, said navigation and tracking assembly comprising at least one of the following:

a robotic arm carrying said plant treatment assembly, and wherein said control system is configured and operable to controllably move the robotic arm in three dimensions;

a ground vehicle configured and operable to controllably transport the plant treatment apparatus to the vicinity of said at least portion of the plant;

at least one of optical and positioning sensors; and an inertial moment unit configured and operable to determine spatial movement path of the robotic arm to thereby optimize plant treatment process time and energy.

22. The plant treatment system according to claim 1, wherein said plant treatment device is mounted on a telescopic arm being controllable by said control system, to thereby adjust distance between said a distal side of said plant treatment device and the at least portion of the plant.

23. The plant treatment system according to claim 1, wherein said at least one plant treatment device is configured and operable as a plant pollination device, said control system is configured and operable to determine, based on said sensing signals, whether at least one flower on said portion of the plant is ready for pollination, by comparing said sensing signals with reference data comprising images of flowers ready for pollination, and/or by processing said image data to identify presence of a flower in the image(s) and identify readiness of the flower(s) for pollination by identifying flower parameters indicative of existence or absence of pollination, and/or by utilizing trained artificial intelligence.

24. The plant treatment system according to claim 1, wherein said plant treatment apparatus has one of the following configurations:

(a) said plant treatment apparatus further comprises a pollination inhibiting device configured and operable to prevent pollination to occur to one or more flowers and/or prevent growth and blossoming of additional flowers within said at least portion of the plant, while minimizing damage to nearby parts of the plant, said pollination inhibiting device comprising a laser device configured and operable to irradiate said at least portion of the plant with predetermined laser parameters to thereby damage said at least portion of the plant;

(b) said at least one treatment device comprising an adjustable opening adapted to generate the flow profile of the air flow being a directional and targeted fluid stream that can be directed towards and induces vibration patterns in specific one or more regions in said at least portion of the plant, said at least one treatment device being configured and operable as a pollination inhibiting device configured and operable to generate said fluid stream with a predetermined high temperature, while maintaining the fluid stream directionality by controlling size of fluid stream exit, to burn one or more regions of said at least portion of the plant and prevent pollination to occur to one or more flowers and/or prevent growth and blossoming of additional flowers within said at least portion of the plant, while minimizing damage to nearby parts of the plant.

25. A plant treatment apparatus, comprising:

at least one plant treatment device comprising one or more treatment channels each configured as a fluid flow channel comprising a fluid flow applicator associated with a controllable fluid valve and a fluid pressure regulator, said fluid flow channel being configured and operable to deliver compressed air to the fluid flow applicator by the controllable fluid valve and to control air pressure by the fluid pressure regulator to generate a controlled air flow having a predetermined profile and being a directional and targeted air flow towards specific one or more regions in at least a portion of a plant being treated, to controllably apply a force field to said at least a portion of the plant, said controllable air flow comprising one or more air pulses, wherein each of said one or more air pulses has certain duration and has a predetermined rise time of the air pressure from a first minimal pressure value to a second maximal pressure value controlled by a speed of opening of the controllable fluid valve and defining frequency content of the pulse and amplitude profile, such that said directional and targeted air flow thereby induces a vibration pattern in the at least portion of the plant, such that the air pulses, inducing said vibration pattern, reach the at least portion of the plant with a predetermined rise time and predetermined amplitude providing the vibration pattern characterized by a plurality of vibration frequencies including vibration frequencies above a predetermined value, to thereby apply treatment to said at least portion of the plant;

a sensing system comprising one or more sensors configured and operable to provide sensing signals indicative of a condition of said at least portion of the plant, said one or more sensors comprising an optical sensor configured and operable to provide the sensing signals indicative of image data of said at least portion of the plant; and a communication utility for data communication with a control system to transmit the sensing signals to the control system and receive from the control system operational data for said at least one plant treatment device, the operational data being indicative of operational parameters of the controllable fluid valve and the fluid pressure regulator of the at least one plant treatment device to apply and/or adjust said force field to minimize expansion of the air pulses so that the air pulses reach the at least portion of the plant with predetermined fast rise time and predetermined amplitude to thereby induce the vibration pattern, characterized by the plurality of vibration frequencies above the predetermined value, corresponding to the treatment for said at least portion of the plant.

26. A plant treatment device for use in a plant treatment apparatus to apply treatment to at least portion of a plant, the plant treatment device comprising:

one or more treatment channels each configured as a fluid flow channel comprising a fluid flow applicator associated with a controllable fluid valve and a fluid pressure regulator, said fluid flow channel being configured and operable to deliver compressed air to the fluid flow applicator by the controllable fluid valve and to control air pressure by the fluid pressure regulator to generate a controlled air flow having a predetermined profile and being a directional and targeted air flow towards specific one or more regions in at least a portion of a plant being treated, to controllably apply a force field to said at least a portion of the plant, said controllable air flow comprising one or more air pulses, wherein each of said one or more air pulses has certain duration and has a predetermined rise time of the air pressure from a first minimal pressure value to a second maximal pressure value controlled by a speed of opening of the controllable fluid valve and defining frequency content of the pulse and amplitude profile, such that said directional and targeted air flow thereby induces a vibration pattern in the at least portion of the plant, such that the air pulses, inducing said vibration pattern, reach the at least portion of the plant with a predetermined rise time and predetermined amplitude providing the vibration pattern characterized by a plurality of vibration frequencies including vibration frequencies above a predetermined value, to thereby apply treatment to said at least portion of the plant;

a sensing system comprising one or more sensors configured and operable to provide sensing signals indicative of a condition of said at least portion of the plant, said one or more sensors comprising an optical sensor configured and operable to provide the sensing signals indicative of image data of said at least portion of the plant; and a communication utility for data communication with a control system to transmit the sensing signals to the control system and receive from the control system operational data, the operational data being indicative of operational parameters of the controllable fluid valve and the fluid pressure regulator of the at least one plant treatment device to apply and/or adjust said force field to minimize expansion of the air pulses so that the air pulses reach the at least portion of the plant with predetermined fast rise time and predetermined amplitude to thereby induce the vibration pattern, characterized by the plurality of vibration frequencies above the predetermined value, corresponding to the treatment for said at least portion of the plant.

* * * * *